(12) United States Patent
Prabhakar et al.

(10) Patent No.: US 8,441,645 B2
(45) Date of Patent: May 14, 2013

(54) POLYMER ANALYSIS CHIP

(75) Inventors: Amit Prabhakar, Patna (IN); Soumyo Mukherji, Kolkata (IN)

(73) Assignee: Indian Institute of Technology Bombay, Mumbai (IN)

( * ) Notice: Subject to any disclaimer, the term of this patent is extended or adjusted under 35 U.S.C. 154(b) by 311 days.

(21) Appl. No.: 12/984,328

(22) Filed: Jan. 4, 2011

(65) Prior Publication Data
US 2012/0170044 A1    Jul. 5, 2012

(51) Int. Cl.
*G01N 21/00* (2006.01)

(52) U.S. Cl.
USPC .......................................... 356/440

(58) Field of Classification Search ............ 356/432, 356/440; 204/451; 436/165
See application file for complete search history.

(56) References Cited

U.S. PATENT DOCUMENTS

2006/0011862 A1* 1/2006 Bernstein ................ 250/461.2
2012/0021525 A1* 1/2012 Fehr et al. ..................... 436/94

OTHER PUBLICATIONS

Salimi-Moosavie, H. et al.,"A Multireflection Cell for Enhanced Absorbance Detection in Microchip Based Capillary Electrophoresis Devices," Electrophoresis, vol. 21, Issue 7, pp. 1291-1299, Apr. 2000.
Verpoorte, E. et al., "A Silicon Flow Cell for Optical Detection in Miniaturized Total Chemical Analysis Systems," Sensors and Actuators B: Chemical, vol. 6, Issue 1-3, pp. 66-70, Jan. 1992.
Xue, Y. and Yeung E. S., "Characterization of Band Broadening in Capillary Electrophoresis due to Nonuniform Capillary Geometries," Analytical Chemistry, vol. 66, Issue 21, pp. 3575-3580, Nov. 1, 1994.
J. El-Ali, K. B. Mogensen, I. R. P. Nielsen, J. P. Kutter, P. Telleman, and A. Wolff, "Integration of polymer waveguides for optical detection in biochemical microsystems", Proc. of μTAS 2002, Nara, Japan, p. 260-262 (2002).
Pierre J. Obeid, Theodore K. Christopoulos, Penelope C. Ioannou, Rapid analysis of genetically modified organisms by in-house developed capillary electrophoresis chip and laser-induced fluorescence system, Electrophoresis 2004, 25, 922-930.
Katsumi Uchiyama, Wei Xu, Jingmiao Qiu, Toshiyuki Hobo, Polyester microchannel chip for electrophoresis—incorporation of a blue LED as light source, Fresenius J Anal Chem (2001) 371 :209-211.
Klaus B. Mogensen, Iamil El-Ali, Anders Wolff and Jorg P. Kutter, Integrated Polymer Waveguides for Absorbance Detection in Chemical Analysis Systems, The 12th International Conference on Solid Slate Sensors. Actuators and Microsystems, Boston, Jun. 8-12. 2003, 694-697.

(Continued)

*Primary Examiner* — Roy M Punnoose
(74) *Attorney, Agent, or Firm* — Brundidge & Stanger, P.C.

(57) ABSTRACT

A microfabricated analysis chip with integrated waveguides for evanescent field absorption detection is provided. Fabrication of the microfluidic device may be performed by micropatterning a layer of photoresist or other suitable material using a single step photoresist process to produce a microchannel and an optical structure (e.g., a U-bend waveguide) in the microfluidic device. The microfluidic device couples a micro-channel network with a waveguide in a collinear fashion to maintain higher path length and incurring little or no scattering, dispersion, and divergence losses. A sample can be passed through the microchannel while light is transmitted through the waveguide. Any change in refractive index as well as change in optical absorbance property of fluid flowing in the microchannel can be detected by detecting changes in light output power (e.g., changes in absorbance). A change in concentration of solution in the microchannel can be determined by detecting a change in light absorbance output.

18 Claims, 15 Drawing Sheets

OTHER PUBLICATIONS

Kyung Won Ro, Kwanseop Lim, Bong Chu Shim, and Jong Hoon Hahn, Integrated Light Collimating System for Extended Optical-Path-Length Absorbance Detection in Microchip-Based Capillary Electrophoresis, Anal. Chem. 2005, 77, 5160-5166.

Suz-Kai Hsiung, Che-Hsin Lin, Gwo-Bin Lee, A microfabricated capillary electrophoresis chip with multiple buried optical fibers and microfocusing lens for multiwavelength detection, Electrophoresis 2005, 5, 1122-1129.

S. K. Khijwania, and B.D. Gupta, "Fiber optic evanescent field absorption sensor with high sensitivity and linear dynamic range," Optics Communications, 152, 259-262, 1998.

S.K. Khijwania, B.D. Gupta, Fiber optic evanescent field absorption sensor: effect of fiber parameters and geometry of the probe, Opt. Quant. Electron. 31 (8) (1999) 625-636.

V.V.R. Sai, Tapanendu Kundu, Soumyo Mukherji, Novel U-bent fiber optic probe for localized surface plasmon resonance based biosensor, Biosensors and Bioelectronics 24 (2009) 2804-2809.

A.G. Mignani, R. Falciai, L. Ciaccheri, Evanescent wave absorption spectroscopy by means of bi-tapered multimode optical fibers, Appl. Spectros. 52 (4) (1998) 546-551.

D. Littlejohn, D. Lucas, L. Han, Bent silica fiber evanescent absorption sensors for near-infrared spectroscopy, Appl. Spectros. 53 (7) (1999) 845-849.

M. Sheeba, M. Rajesh, C.P.G. Vallabhan, V.P.N. Nampoori, P. Radhakrishnan, Fibre optic sensor for the detection of adulterant traces in coconut oil, Meas. Sci. Technol. 16 (11) (2005) 2247-2250.

Santeri Tuomikoski, Sami Franssila, Free-standing SU-8 microfluidic chips by adhesive bonding and release etching, Sensors and Actuators A 120 (2005) 408-415.

Manoj Joshia, Richard Pintob, V. Ramgopal Raob and Soumyo Mukherji, Silanization and antibody immobilization on SU-8, Applied Surface Science 253 (2007) 3127-3132.

Manoj Joshi, Nitin Kale, Rakesh Lal, V. Ramgopal Rao, Soumyo Mukherji, A novel dry method for surface modification of SU-8 for immobilization of biomolecules in Bio-MEMS, Biosensors and Bioelectronics 22 (2007) 2429-2435.

S. Qi, X. Liu, S. Ford, J. Barrows, G. Thomas, K. Kelly, A. McCandless, K. Lian, J. Goettert, and S.A. Soper: Microfluidic devices fabricated in poly(methyl methacrylate) using hot-embossing with integrated sampling capillary and fiber optics for fluorescence detection. Lab on a Chip, vol. 2, 2002, pp. 88-95.

S. Camou, H. Fujita, and T. Fujii: PDMS 2D optical lens integrated with microfluidic channels: principle and characterization. Lab on a chip, vol. 3, 2003, pp. 40-45.

K.W. Ro, CH., B, Shim, K. Lim, and J.H. Hahn, Integrated Light Collimating System for Extended Optical-Path-Length Absorbance Detection in Microchip-Based Capillary Electrophoresis, Anal. Chem. 2005, 77, 5160-5166.

Z. Liang, N. Chiem, G. Ocvirk, T. Tang, K. Fluri, and D.J. Harrison: Microfabrication of planar absorbance and fluorescence cell for integrated capillary electrophoresis devices. Analytical Chemistry, vol. 68, No. 6, 1996, pp. 1040-1046.

L Cui, T. Zhang, and H. Morgan: Optical particle detection integrated in a dielectrophoretic labon-a-chip. Journal of Micromechanics and Microengineering, vol. 12, 2002, pp. 7-12.

K.B. Mogensen, N. J. Petersen, J. Hübner, and J.P. Kutter: Monolithic integration of optical waveguides for absorbance detection in microfabricated electrophoresis devises. Electrophoresis, vol. 22, 2001, pp. 3930-3938.

J. Hübner, K.B. Morgensen, A.M. Jorgensen, P. Friis, P. Telleman, and J.P. Kutter: Integrated optical measurement system for fluorescence spectroscopy in microfluidic channels. Review of Scientific Instruments, vol. 72, 2001, pp. 229-233.

Denninger et al., "Absorbance Detection in Microsystems: Microcuvette and Waveguide Approach", Eurosensors XIV, 2000, pp. 457-558.

* cited by examiner

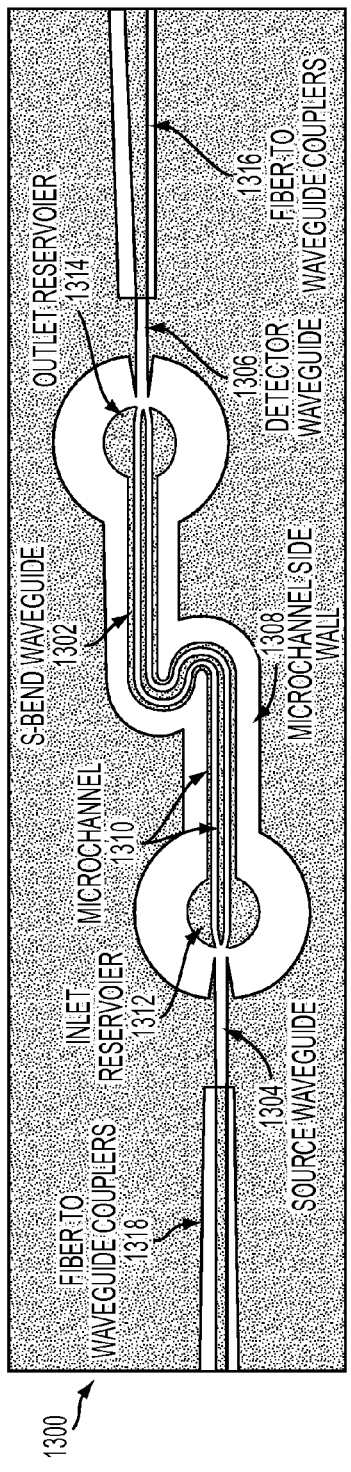
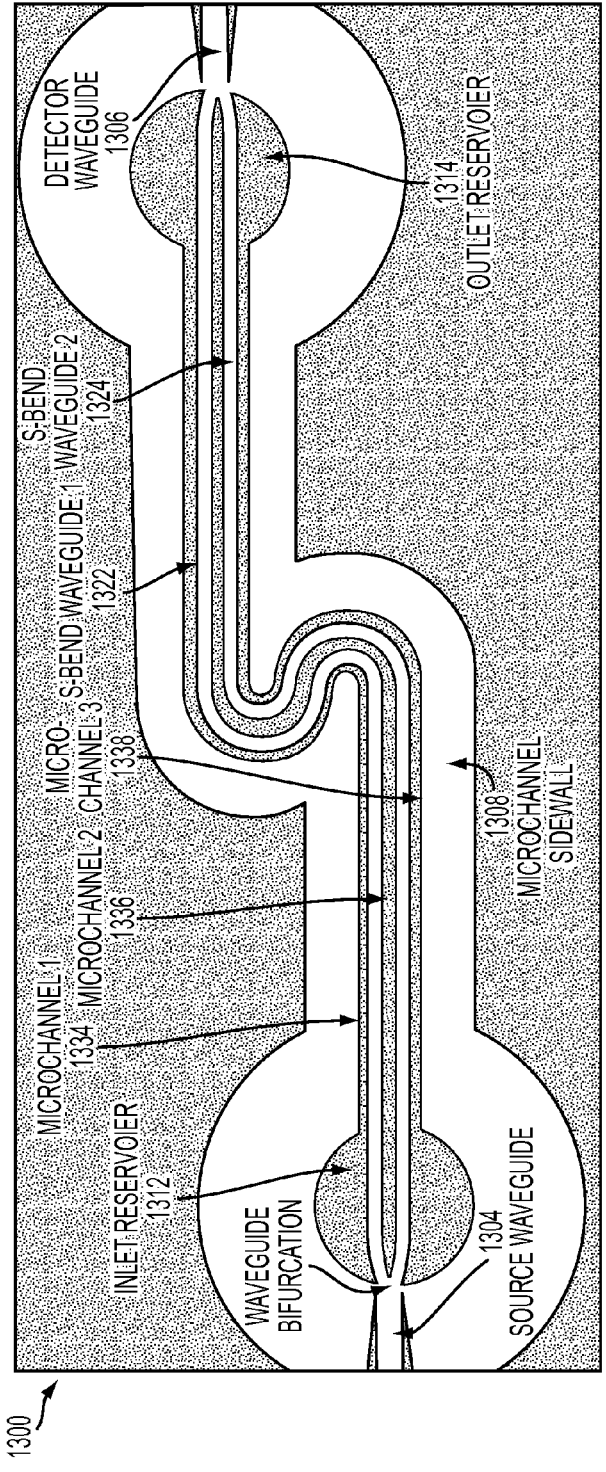
FIG. 13A
FIG. 13B

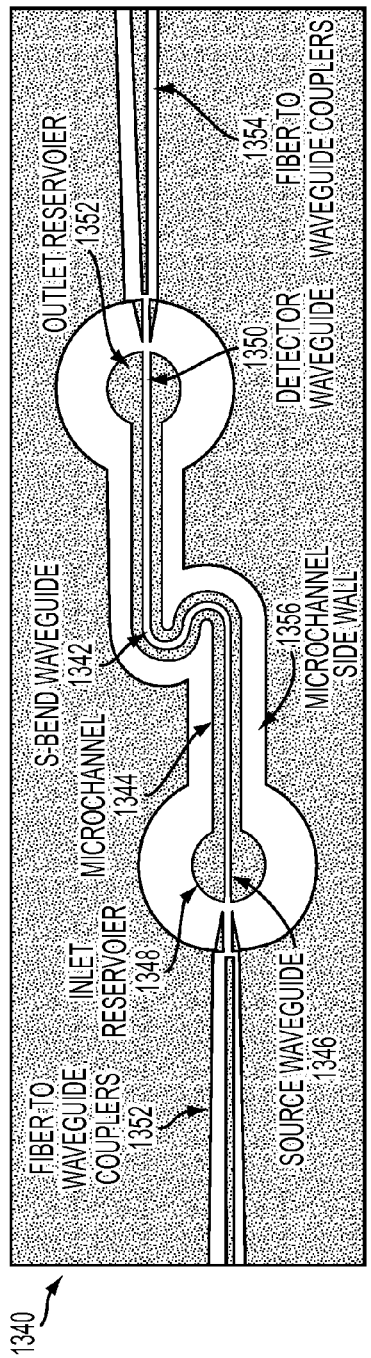
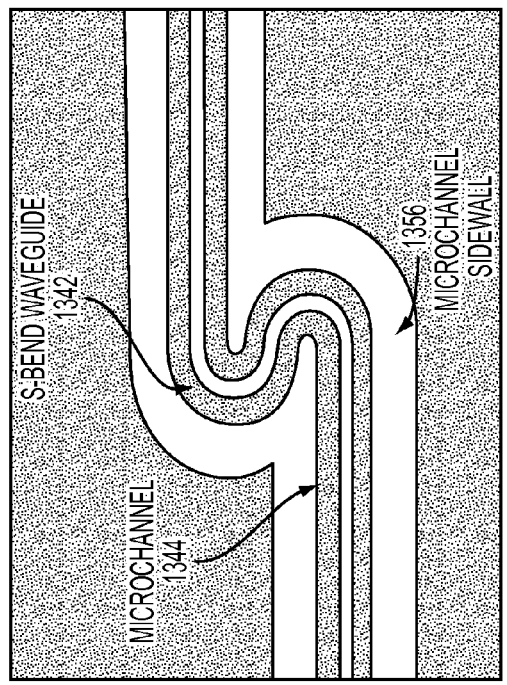
FIG. 13C
FIG. 13D

POLYMER ANALYSIS CHIP

BACKGROUND

Separation or detection of ionic species is generally performed based on the electrochemical properties of analytes. Capillary electrophoresis (CE) is an analytical separation technique for analysis of a sample performed in a narrow diameter microchannel or capillary tube, which is filled with an electrically conductive medium (e.g., electrolyte). In electrophoresis, electrically charged analytes move in the electrolyte of the capillary under the influence of an electric field. CE can be used to separate ionic species by their charge, frictional forces, and mass so as to separate species based on their size-to-charge ratio. For example, ionic species in the sample move from one electrode toward another at a rate that is dependent upon certain characteristics, such as molecular charge, size and/or mobility.

CE may be performed using gels or liquids, such as buffers, in the capillary. For example, CE can also be used with fluorescence detection to obtain a high separation resolution, and good signal-to-noise ratios using integrated fluorescence detection optical elements. As compared to electrochemical detection techniques, fluorescence detection techniques are comparatively free from high separation voltage interferences. However, fluorescence detection may require sample to be fluorescent or made fluorescent by virtue of a suitably attached tag. This requires some chemical treatment that leads to the possibility of alteration of physical and chemical characteristics of the target molecule.

An alternative technique for detection without modifying the sample is optical absorbance. For absorbance detection, ultraviolet (UV)-visible range light is used because biomolecules have significant absorption at such wavelengths. Absorption based detection uses a light path across a microchannel cross section, and may be limited by a path length in terms of sensitivity and detection resolution and scattering of light as the light passes through the microchannel. Microlenses may be used to focus the light into the microchannel and collecting the light at a detector.

Evanescent light wave absorbance based techniques may also be used in which the sample interacts with the evanescent field of light traveling along a waveguide (optical fiber). The interaction induces changes in absorbance characteristics between a source and a detector placed at opposite ends of the waveguide.

Optical detection methods may have a broad application in analytical biology and chemistry. Optical coupling of microfluidic elements in microstructure analytical devices can be performed for use in optical detection methods. Microfluidic channels may need to be hermetically sealed, and a location and position of optical fibers can result in complex designs that are difficult to manufacture.

SUMMARY

In one aspect, an example microfluidic device is provided that comprises an optical waveguide and a microchannel. The optical waveguide comprises a first substantially linear section, a substantially semi-circle section having a first end coupled to the first substantially linear section, and a second substantially linear section coupled to a second end of the substantially semi-circle section. The optical waveguide receives an optical beam via the first section and guides the optical beam through the substantially semi-circle section to the second section. The microchannel is adjacent the optical waveguide and has a pathway defined by a shape of the optical waveguide. A sample medium in the microchannel absorbs a portion of an evanescent field of the optical beam that extends from the substantially semi-circle section and decreases an intensity of the optical beam.

In another aspect, an example method of fabricating a microfluidic device is provided. The method comprises applying a photoresist material onto a surface of a substrate in a pattern to form an optical waveguide and a microchannel adjacent the optical waveguide. The pattern of the optical waveguide comprises a first substantially linear section, a substantially semi-circle section having a first end coupled to the first substantially linear section, and a second substantially linear section coupled to a second end of the substantially semi-circle section. The pattern of the microchannel is defined by a shape of the optical waveguide. The pattern defines both the microchannel and the optical waveguide in the microfluidic device so that a single photoresist step is used to define the microchannel and optical waveguide. The method also includes applying a sheet of material to the substrate to seal the substrate.

In still another aspect, a method of detection of an analyte using a microfluidic device is provided. The method comprises passing a sample through a microchannel of the microfluidic device, and transmitting light through an optical waveguide that is adjacent a portion of the microchannel. The optical waveguide comprises a first substantially linear section, a substantially semi-circle section having a first end coupled to the first substantially linear section, and a second substantially linear section coupled to a second end of the substantially semi-circle section. The optical waveguide receives the light via the first section and guides the light through the substantially semi-circle section to the second section. A pathway of the portion of the microchannel is defined by a shape of the substantially semi-circle section. The method also includes detecting a change in light output power at an end of the second substantially linear section due to absorbance of a portion of an evanescent field of the light that extends from the substantially semi-circle section decreasing an intensity of the light, and determining a concentration of the sample in the microchannel based on the change in light output power.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIGS. 13A-E illustrates an example mask design of a microfluidic device that couples optical and microfluidic elements.

DETAILED DESCRIPTION

Figure 1:
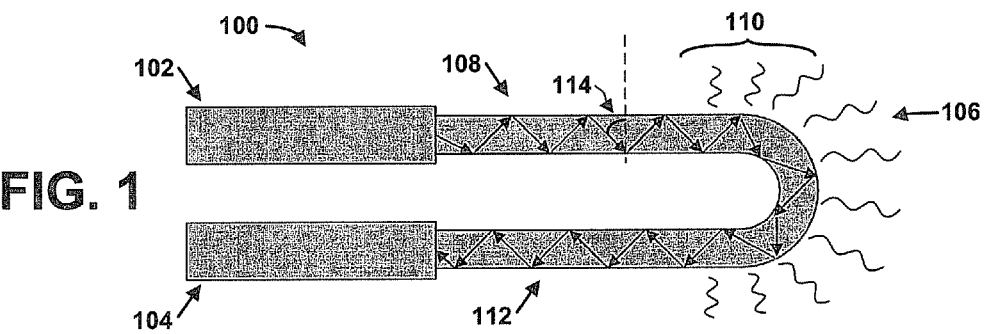
FIG. 1 illustrates an example U-bend waveguide.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

An example microfluidic device for evanescent field absorption detection using integrated polymer waveguides is provided. The evanescent field absorption detection is a form of label free detection in that the sample is not required to have any fluorescent (or other) label. Fabrication of the microfluidic device may be performed using a single step photoresist process to produce a micro-channel and an optical structure (e.g., such as a U-bend waveguide) into the microfluidic device. The microfluidic device couples a microchannel network with a U-bend waveguide in a collinear fashion to maintain higher path length with incurring little or no scattering, dispersion, and/or divergence losses.

In example embodiments, the waveguide includes a U-bend configured for increasing depth of penetration of light as evanescent fields, for example. Channel widths of microchannels may be about 20 μm to about 500 μm. In some embodiments, the widths may be about 20 μm to about 250 μm, 20 μm to about 100 μm, 20 μm to about 50 μm, 50 μm to about 500 μm, 50 μm to about 250 μm, or 100 μm to about 500 μm. Channel width may be of any other range of size, ranging from a minimum size for evanescent wave penetration depth and a maximum of any required width. A sample can be passed through the microchannels while light is transmitted through the U-bend waveguide. Changes in refractive index of fluid flowing in the microchannels can be detected by detecting a change in light output power such as a change in light intensity coming out of the U-bend waveguide. A change in concentration of solution in the microchannels can be determined by detecting a change in light absorbance output through the U-bend waveguide.

In example embodiments, the microfluidic device may be applicable for evanescent absorbance measurements at wavelengths of about 450 nm to about 780 nm, although the microfluidic device may be applicable for evanescent absorbance measurements at a broader range of wavelengths for applications using other optical power absorbing spectrums. As an example, a spectrum of transmittance in the waveguide may be modified based on materials used for fabrication of the microfluidic device. A percentage change in optical absorbance depends upon a molar extinction coefficient of an analyte as well as a depth of penetration of evanescent waves and length of analyte interaction, for example.

The microfluidic device may also be sensitive to a refractive index of fluid flowing in the channels, for example. A change in refractive index causes a change in an angle of core cladding interface, i.e., a change a TIR (Total Internal Reflection) condition. An increase or decrease of the angle results in an increase or decrease in losses due to refraction of higher order modes of transmitted light. In further example embodiments, the microfluidic device may also be used as an optical sensor for identification and quantification of various molecular interactions. For detection of specific molecules or bio-molecules, a waveguide of the microfluidic device can be coated with respective receptor or bioreceptor molecules. The bioreceptor molecules can bind with the waveguide surface molecules and a corresponding sample (e.g., complementary bio-analyte molecule that is recognized by or fits on the surface of the bioreceptor molecule) can be provided in microfluidic channels of the microfluidic device. The bio-analyte may be in contact with the coated or bioreceptor immobilized surface for interaction in the evanescent field region. For instance, the evanescent waveguide has a depth of penetration (i.e., a region into which the field exists), and interaction/binding of a bioreceptor and bioanalyte in this region causes absorption of the evanescent power due to absorbing bioanalyte molecules, which may lead to a change in light intensity output coming out of the waveguide. In this embodiment, the waveguide may be embedded in the microchannel (e.g., the waveguide may be part of the microchannel such as part of the microchannel wall) and the bioreceptor can be immobilized on the waveguide, in the channel, or on the channel walls for biosensing purposes.

Furthermore, a waveguide can also be used for the same purpose without a specific microchannel with the analyte in contact with the waveguide, for example. Because the U-bend waveguide is a sensing element of the microfluidic device, the U-shaped waveguide can be used alone without an embedded microchannel. In still further example embodiments, the microfluidic device may also be used as a detection component in various electrophoresis based Lab-On-Chip devices such as optical detection based sensors.

In example embodiments, the microfluidic device takes the form of a micro total analysis system (μ-TAS) for evanescent field absorption with integrated polymer waveguides. Absorbance measurements were performed by passing various concentrations of dye solutions within micro-channels of the microfluidic device. The device was also found to be sensitive to refractive indices of fluid flowing in the microchannels. The refractive index sensitivity was tested by flowing various refractive index sucrose solutions in the microchannels and measuring absorbance across the waveguide. Molecules or compositions that have light absorption properties in a range of wavelengths (for example, about 450 nm to about 780 nm) can be detected, and a change in refractive index of fluid in the microchannel with respect to a reference fluid (i.e., deionized water) can be determined by calculating a change in intensity output of the waveguide with respect to the reference fluid. Bioanalyte molecule binding to waveguide surface immobilized bioreceptor molecules can cause changes in the refractive index around the waveguide leading to a change in intensity output.

Referring now to the Figures, FIG. 1 illustrates an example U-bend waveguide 100. Light is transmitted through the U-bend waveguide 100 from a source that provides light through a portion 102 (e.g., a cladded optical fiber portion) of the waveguide 100. A detector coupled to a portion 104 (e.g., a cladded optical fiber portion) of the waveguide 100 is present at an opposite end of the U-bend waveguide 100, and may determine an intensity of light at the opposite end. When light is transmitted through the U-bend waveguide 100, as illustrated by the arrows within the U-bend waveguide 100, light reflects off of interiors walls of the U-bend waveguide 100. In addition, a small portion of reflected light penetrates through the walls of the U-bend waveguide and creates an electromagnetic field or evanescent field 106 into a surrounding medium adjacent to the U-bend waveguide 100. The evanescent field 106 may be present around other areas of the U-bend waveguide 100 as well, including around the straight and curved portions.

The U-bend waveguide 100 is an example of an optical waveguide that guides light or optical beams through the waveguide, and may comprise optical fibers or polymers. The optical waveguide may comprise any transparent organic or inorganic materials (i.e., transparent for any detection wavelength) that can be micropatterned, and evanescent wave absorption depends upon a particular wavelength transmitted through the waveguide. For non-limiting example, polymethyl methacrylate (PMMA), polydimethylsiloxane (PDMS), glass, polystyrene, or polypropylene can be used for optical waveguide fabrication.

The U-bend waveguide 100 includes a first substantially linear section 108, a substantially semi-circle section 110 (or U-bend region) that has an end coupled to the first linear section 108, and a second substantially linear section 112 coupled the other end of the semi-circle section 110. An optical beam of light is received via the first linear section 108 and is guided through the semi-circle section 110 to the second linear section 112. The semi-circle section 110 is configured as a U-shape, for example, and has an arc or curvature of about 180°. The arc or curvature may be of any curvature depending upon requirements of users. For example, for biosensor based applications, a U-shaped outer periphery of a U-bend waveguide may be selected for high sensitivity, and thus, an arc curvature of 180° may be used. As another example, for design of an electrophoretic separation based chip, an arc of curvature less than 180° (for example, 90° curvature) can be used to lower diffusion between electrophoretic analyte bands (after electro separation) due to a U-shaped channel design.

The semi-circle section 110 may be configured as half of a circle, for example, and may be configured to curve inward or outward depending on a configuration of the U-bend waveguide 100. Portions of the U-bend waveguide 100 (e.g., such as any of the first linear section 108, the semi-circle section 110, or the second linear section 112) may have a width of about 200 μm. The width can be of any other size, and sensitivity is approximately inversely proportional to waveguide width or diameter. Thus, thinner width waveguides may improve sensitivity. Widths of a waveguide may also be considered for strength of the waveguide (e.g., for bonding purposes during micro-channel sealing). The semi-circle section 110 may have a curvature diameter of about 1 mm. The curvature diameter can be other sizes or ranges of sizes, and sensitivity is approximately inversely proportional to a bending diameter.

In an embodiment, the evanescent field 106 extends deeper into surrounding medium at the semi-circle section 110 than at the first linear section 108 or the second linear section 112. A strength (e.g., energy per unit area per second) of the evanescent field 106 at the semi-circle section 110 allows changes to occur in analytes present in the surrounding medium. The analyte can be any molecule with optical absorption property (in a range of wavelength transmitted in the waveguide, for example). For example, if analytes absorb a portion of light of a particular wavelength that is present or provided, then an intensity of light at the detector 104 decreases because less light will be detected at the detector 104. Light absorbance in the semi-circle section 110 is proportional to a concentration of analytes in the surrounding medium. Experimental evanescent absorbance was found approximately proportional to the range of concentration of the analytes.

Light absorption can be generally described by Lambert-Beer's law. For example, absorbance of light in a uniform-core (e.g., straight configuration) decladed optical fiber can be explained by Lambert-Beer's Law, shown below in Equation (1).

$$A = \alpha L \eta \quad \text{Equation (1)}$$

Where L is a length of interaction, $\eta$ is a fraction of light in the evanescent field, and $\alpha$ is an absorption coefficient. The absorption coefficient can be determined using Equation (2) below.

$$\alpha = \epsilon C \quad \text{Equation (2)}$$

Where C is a concentration of the analytes and $\epsilon$ is a molar absorptivity.

The equation for Sensitivity (S) is shown below in Equation (3).

$$S = \epsilon L (\eta + C (\partial \eta / \partial C)) \quad \text{Equation (3)}$$

Sensitivity refers to change in evanescent wave absorbance per unit change in concentrations of analyte. For species with weakly absorbing property, sensitivity can be approximated as shown below in Equation (4).

$$S = \epsilon L \eta \quad \text{Equation (4)}$$

In a uniform-core optical fiber, $\eta$ is significantly low. For example, in a 200 um diameter fiber, $\eta$ is about $10^{-4}$.

To enhance the sensitivity, bends and tapered ends may be used in the waveguides, such as using a configuration like the U-bend waveguide 100. As shown in FIG. 1, in the semi-circle section 110, as an incident angle 114 of a guided ray decreases, it leads to an increase in penetration depth into the external medium. In addition, bending of the waveguide causes higher order waveguide propagation modes (e.g., propagating lights of differing wavelengths) to occur, which leads to a higher percentage of power in the evanescent field 106. For example, in any bend portion of a waveguide, an angle of incidence decreases as compared to a straight portion of waveguide. This decrease leads to a higher depth of penetration of evanescent field in the bent regions, which indicates higher power in evanescent field. A higher power in the evanescent field indicates a loss of power from the waveguide, and the loss of power can be detected by the power output from the waveguide.

A magnitude of the evanescent field 106 that propagates depends on a numerical aperture of the waveguide 100 (e.g., range of angles over which the waveguide 100 can accept or emit light). An optical fiber has a numerical aperture of about 0.38 and the waveguide has a refractive index (RI) of about 1.59 and air cladding that provides a numerical aperture of about 1.23. A higher numerical aperture indicates a lower loss due to refraction in the waveguide. The numerical aperture depends upon a difference between a refractive index of a core of the waveguide 100 and the sample. Example fibers may have a core refractive index of about 1.457 and a clad refractive index of about 1.404 to provide an angle of curvature of the fiber of about 75°.

Geometric parameters, such as a bending radius, can also affect the sensitivity of the waveguide 100. For example, geometric parameters, such as a bending radius or a waveguide diameter, may affect a depth of penetration of evanescent field and sensitivity. Further, in an application using tapered optical fiber sensors, a taper ratio and taper profile may also affect the sensitivity.

Figure 2A:
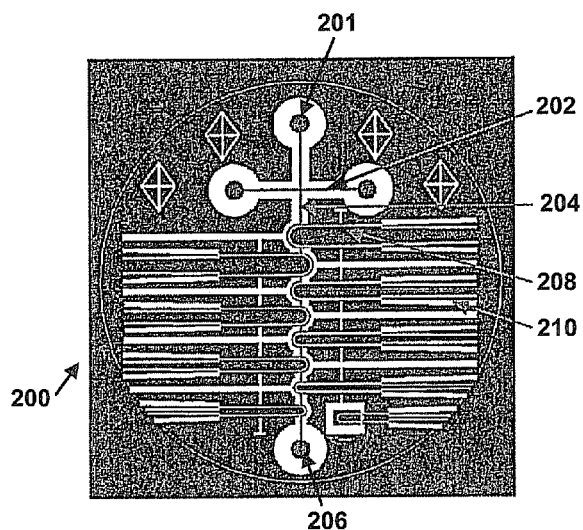
FIGS. 2A-2B illustrate an example mask design of a microfluidic device that couples optical and microfluidic elements.
Figure 2B:
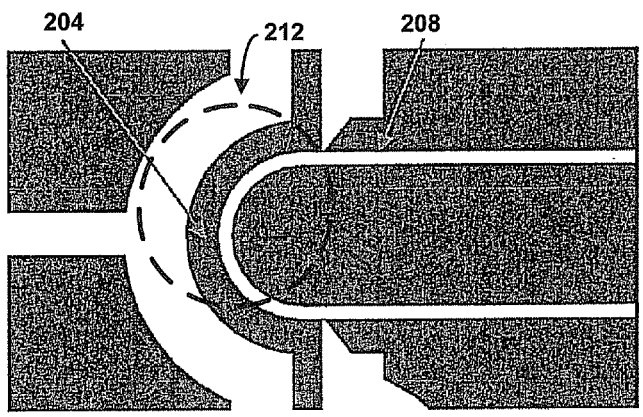

FIGS. 2A-2B illustrate an example mask design of a microfluidic device 200 that couples optical and microfluidic elements. The microfluidic device 200 includes an inlet reservoir 201 that receives a sample. The inlet reservoir 201 may comprise the same materials as a microchannel or waveguide (e.g., SU-8 photoresist, or any photo-resist that includes optical transmittance properties such as PMMA) because all microstructures of the microfluidic device 200 may be patterned from a spin coated SU8 layer in a single step fabrication procedure, for example. A periphery of the inlet reservoir 201 may be circular with a diameter of about 2 mm to about 3 mm. Samples inserted into the inlet reservoir 201 can be any bio-analyte, organic or inorganic fluid samples with an optical absorbance (for evanescent absorbance based detection) or a transmittance property (for RI detection based detection), for example.

The inlet reservoir 201 is connected to an injection microchannel 202 that couples to a separation microchannel 204. The inlet reservoir 201, the injection microchannel 202, and the separation microchannel 204 may all comprise the same material (e.g., SU-8 photoresist). The inlet reservoir 201, the injection microchannel 202 and the separation microchannel 204 may be inter-connected so that a sample can flow through these regions via movement of the microfluidic device 200, for example. The separation microchannel 204 leads to a waste reservoir 206, and is adjacent a U-bend waveguide 208. The waste reservoir may be circular in shape and may have about a 2 mm to about a 3 mm inner diameter. The waste reservoir may alternatively be of any shape (i.e., rectangular, square, semicircular, etc.) and of any diameter according to design requirements. A diameter, area, or volume of the waste reservoir may depend upon an amount of analyte volume available for analysis and ease of integrating inlet and outlet tubes. Smaller diameters (for example, up to micrometer range) may be suitable for small sample volumes, and larger diameters (for example, up to millimeter range) may be suitable for manually integrating inlet and outlet tubes into the reservoir. Although described as separate parts or components of the microfluidic device 200, any of the inlet reservoir 201, the injection microchannel 202, and the separation microchannel 204 may be integral components, and thus, may be the same channel within the microfluidic device 200, for example.

The injection microchannel 202 and the separation microchannel 204 are defined by microchannel sidewalls. The sidewalls may comprise a polymer SU-8, for example, and a width of a sidewall in a region for sensing (e.g., in a region 212) may be about 200 micron. Widths of sidewalls may be about 1 mm to about 2 mm in other regions of the microchannel 202. An outer sidewall of the U-bend waveguide 208 may form a sidewall of the separation microchannel 204. The separation microchannel 204 is adjacent the U-bend waveguide 208 and has a pathway defined by a shape of the U-bend waveguide 208, for example. In an example embodiment, widths of the injection microchannel 202 and the separation microchannel 204 may be about 20 µm to about 500 µm, for example. Any of the microchannels may have a square or rectangular cross section, for example. The microchannels may have other shapes as well, such as round or oval.

The microfluidic device 200 is shown including a number of microchannels and eight U-bend waveguides, however, more or fewer waveguides may be included, for example. A number of waveguides included in the microfluidic device 200 may depend on an application of the microfluidic device 200. For example, different bioreceptor molecules can be immobilized on different waveguides, and during passage of a sample analyte in a microchannel, a corresponding bioanalyte will bind to complementary immobilized biomolecules in the waveguide and evanescent absorbance across the waveguide may confirm qualitative and quantitative information of the sample analyte. Because the U-bend waveguide may be a wall of the microchannel, when bioanalytes bind to immobilized biomolecules over the waveguide, the bioanalytes come into the evanescent wave region of the U-shaped waveguide and further absorb evanescent waves causing a change in light intensity output of the waveguide. The absorption properties of the bioanalyte will determine an amount of change in intensity output of the waveguide. The number of waveguides may also depend upon requirements of a user. In the example shown in FIG. 2, a design is illustrated that provides a number of different bending diameter waveguides included in a substrate region. The separation microchannel 204 has a pathway defined by U-bend regions of each of the U-bend waveguides, for example.

To couple light into the microfluidic device 200, fiber-to-waveguide couplers 210 are connected to the U-bend waveguide 208 to couple a light source and detector to the U-bend waveguide 208 through optical fibers. The light source may be an LED, a laser diode or laser beam, for example. The detector can be a spectrophotometer, photodiodes, avalanche photodiodes, or a photomultiplier tube, for example. The fiber-to-waveguide couplers 210 may include a tapered groove that is inserted into the U-bend waveguide 208 to ensure alignment with the U-bend waveguide 208.

The coupling of light to the waveguide can also be performed by focusing a light beam into an end of the waveguide 208 using opto-mechanical components. The fiber to waveguide couplers 210 may be a hollow structure that has a wider cross sectional aperture (e.g., twice the waveguide cross sectional dimension) at a site of insertion and a same cross sectional dimension (e.g., same as waveguide cross sectional dimension) at an interface to an input and output of the U-bend waveguide 208. The fiber to waveguide couplers 210 may couple incident and outgoing light from the U-bend waveguide 208 from and to a source and a detector, respectively, for example.

FIG. 2B illustrates a magnified view of the separation microchannel 204 and U-bend waveguide 208 configuration. In this example, the U-bend waveguide 208 follows the same form and shape of the separation microchannel 204 in a region 212.

In example embodiments, methods of molecule detection can be performed by inserting a sample at the inlet reservoir 201 or the injection microchannel 202 and passing the sample through the separation microchannel 204 while light is transmitted through the U-bend waveguide 208. The inlet reservoir 201 may include inlet tubes and outlet tubing that can be used respectively for introducing and removing the sample. The sample can be injected into the tubing using for example, a syringe, and injection may further drive the sample to and through the microchannels. For example, introduction of a sample into inlet tubing causes the sample to flow into the inlet reservoir 201, microchannel 202, the U-bend waveguide 208, and into an outlet reservoir. Injection may be performed manually by filing a syringe with a sample, and pushing a needle of the syringe into the inlet tubing to inject the sample into the inlet tubing. The sample can also be introduced in a controlled manner into the inlet tubing using a syringe pump or other micropump. Any change in refractive index of fluid flowing in the separation microchannel 204 can be detected by detecting a change in light output power (e.g., a change in absorbance measured with a spectrophotometer) at an end of the U-bend waveguide 208 as compared to previous measurements, for example. A change in concentration of a solution in the separation microchannel 204 compared to previous measurements or known values can be determined by detecting a change in light absorbance output through the U-bend waveguide 208.

In spectroscopy, absorbance A (also called optical density) is defined as:

$$A_\lambda = -\log_{10}\left(\frac{I}{I_o}\right) \quad \text{Equation (5)}$$

where I is intensity of light at a specified wavelength λ that has passed through a sample (e.g., transmitted light intensity) and $I_0$ is intensity of light before entering the sample or incident light intensity (e.g., power). Because the absorbance is a ratio of intensity of transmitted and incident light, absorbance is a unit-less quantity. In example embodiments, $I_0$ can be taken as the intensity output of the waveguide when zero concentration of analyte (i.e., deionized water) is present in the microchannel and I can be taken as the intensity output of the waveguide when sample analyte of various concentrations is present in the waveguide. A spectrometer can be used for determination of absorbance, for example.

The example U-bend waveguide 208 may be continuous and collinear with the separation microchannel 204 (in the U-bend region) to reduce optical losses due to divergence and dispersion of light as well as to maintain higher path length. For example, the U-bend waveguide 208 follows the same form and shape as the separation microchannel 204 in a region 212 (shown in FIG. 2B) where light from the U-bend waveguide 208 interacts with the separation microchannel 204. The U-bend waveguide 208 further enables increasing a depth of penetration, for example, by approximately ten times (as compared to a straight waveguide) of the evanescent field of light into the solution in the separation microchannel 204. Scattering of light due to transition from one medium to another (e.g., waveguide to sample to waveguide) is reduced or eliminated using this configuration. For example, in an instance in which the U-bend waveguide 208 is discontinuous, a microchannel lies between two linearly aligned waveguides, and a change in microchannel analyte properties may lead to a change in light absorbance patterns across two waveguides.

The microfluidic device 200 may be used for sensing various types of molecules including bio-molecules, gas molecules, molecular interactions, etc. The microfluidic device 200 can be used to detect small changes (e.g., sensitivity on the order of $10^{-5}$ RI) in refractive index of fluid flowing in the separation microchannel 204. Various bio-molecular interactions, such as but not limited to antigen-antibody interactions, DNA hybridization, pathogen antibody interactions, enzyme substrate interactions, etc. lead to changes in refractive indices around a waveguide surface, and thus, the microfluidic device 200 can be used for identification and quantification of various bio-molecular interactions, for example.

As an example, a bioreceptor molecule can be immobilized on a surface of the waveguide (as described above) and binding of corresponding bio-analyte molecules may cause a change in RI condition of the surface of the waveguide resulting in a change in an incident angle and further the intensity output. In another example, if a bio-analyte molecule is tagged with a fluorescent molecule, the bioreceptor analyte binding may lead to an increase in evanescent absorbance across the waveguide and further decrease intensity output. Thus, the bio-molecular interactions can be identified.

As another example, interaction of antibody HIgG (Human immunoglobine G) immobilized on a surface of the waveguide and bio-analyte FITC tagged GaHIgG (Goat anti Human immunoglobine G) flowing in the micro-channel may cause an increase in RI of the surface of the waveguide as well as an increase in evanescent wave absorption across the waveguide. This may further lead to a change in intensity output of the waveguide.

Figure 3A:
FIGS. 3A-3F are block diagrams that illustrate fabrication of a microfluidic device.

FIGS. 3A-3F are block diagrams that illustrate fabrication of a microfluidic device. As shown in FIG. 3A, a substrate 300 is used as a base for the microfluidic device. The substrate 300 may be a silicon substrate. Alternatively, the substrate may be any substrate having an RI lower than the RI used for the waveguide (e.g., a substrate such as but not limited to glass, PMMA, PDMS, etc.). The substrate 300 may be of about 2 inches (about 5.08 cm) in diameter with a thickness of about 275 μm.

Figure 3B:
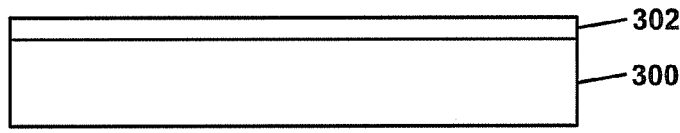

As shown in FIG. 3B, an oxide layer 302 may be grown on the substrate 300 using wet oxidation methods. For example, a silicon wafer may be heated at about 900° to about 1200° C. in atmosphere containing oxygen and hydrogen or water vapor, and thus, the oxide layer may be a layer of silicon dioxide. Alternatively, in place of the oxide layer 302, there may be any other material having a refractive index (RI) lower than that used for the waveguide (e.g., PDMS, PMMA, polypropylene, polytetrafluoroethylene (PTFE), polystyrene etc.) of a thickness of about 1 μm. The oxide layer could alternatively be of a thickness of about 1 micron to about 200 microns, for example. If substrates that have a lower RI than the waveguide are used (e.g., glass, PMMA, PDMS, etc.), then the oxide layer 302 may be omitted. The oxide layer 302 may serve as an underlying layer for a waveguide, and thus, the oxide layer 302 may have values of n=1.458 at 635 nm, for example. The substrate 300 is thus wet oxidized using a silicon substrate layer, for example.

Figure 3C:
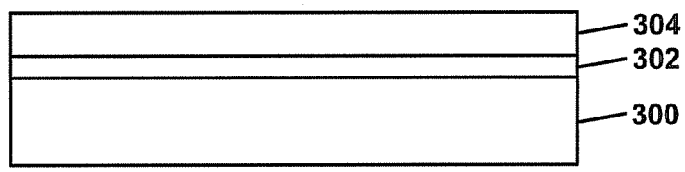

As shown in FIG. 3C, a layer of a photoresist material 304 may be formed on a surface of the oxide layer 302. An example photoresist material includes, but is not limited to SU-8 (e.g., SU-8-2100, available from Microchem, U.S.A., η=1.59 at 635 nm). Alternate types of materials may also be used including photoresist materials that may be a patterned or optically transparent polymers, for example. For example, PMMA or UV curable transparent glue can be used. A transparent inorganic (i.e., glass, silicon, nitride, spin on glass) or organic (i.e., polystyrene, polycarbonate) polymer can be etched by various DRIE or RIE etching processes into a pattern using a mask. In this example, transparent polymers can be coated and dried or deposited over a substrate. Further, a positive photoresist (PPR) can be coated and patterned over the transparent polymer layer using the same mask. The underlying transparent polymer can be etched in the same PPR pattern using DRIE or RIE techniques. For the photo-pattern able transparent polymers (i.e. SU8, PMMA) a single step photoresist process can be used to define both the optical and channel-fluidic structures of the microfluidic device. The photoresist material may be a thickness of about 150 μm, or alternatively may be of any other thickness ranging from about a few microns to about a few millimeters, and may be spin coated a predetermined rotation per minute speed, for example, such as at 1500 rpm onto the oxide layer 302 to form a coating.

Figure 3D:
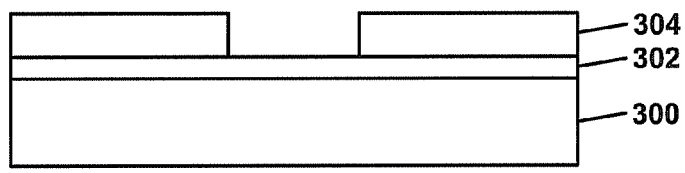

Next, as shown in FIG. 3D, the photoresist material 304 may be patterned according to any desired pattern, and as shown in FIG. 3D, portions of the layer of the material 304 are removed to form a pattern. Different patterns may be made including patterns having microfluidic channels of about 200 μm and about 500 μm, for example, and patterns including but not limited to those as illustrated in FIGS. 2A-2B. The patterned coating 304 may thus comprise a photoresist material that is a light-sensitive coating applied to the oxide layer 302, exposed, and developed. Exposed areas may thus comprise patterns, for example, a U-shaped waveguide, of the microfluidic channels and waveguide to optical fiber couplers structures. Using the mask design, various other transparent non-photoresist patternable materials (e.g., PDMS, glass, polystyrene, etc.) can be patterned into a specific patterns (i.e., U-shaped waveguide, the microfluidic channels and waveguide to optical fiber couplers structures) using micro-fabrication processes, such as, wet etching, reactive ion etching (RIE) etching, deep reactive ion etching (DRIE) or high power laser ablations, for example.

Figure 3E:
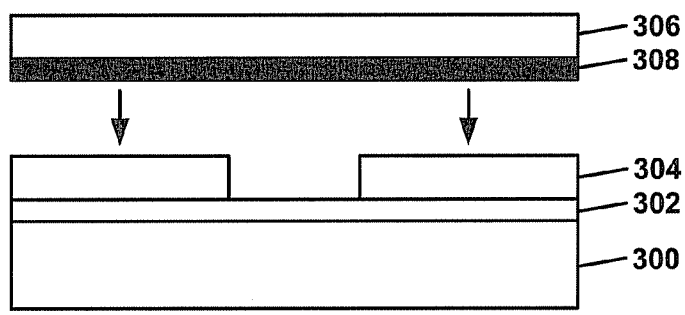
Figure 3F:
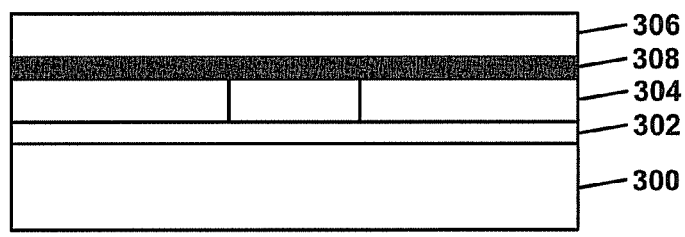

Following, as shown in FIG. 3E, the patterned coating 304 may be sealed with a sheet of material 306 that may be about 200 um to about 2 mm thick. For example, the sheet of material 306 may be a poly(methyl methacrylate) (PMMA) sheet using polydimethylsiloxane (PDMS) as an intermediate layer. The sheet of material 306 may alternatively comprise any solid hard or soft inorganic or organic material (e.g., polymer, metal or glass sheet). The sheet of material 306 may include drilled holes to correspond to reservoirs, such as four reservoirs (more or fewer reservoirs may also be included), for example. The sheet of material 306 may be spin coated with a PDMS layer 308, which may alternatively be any polymer material that can be spin coated into the substrate in a liquid state and can be cured to a hard solid insoluble material by a chemical or physical means. For example, epoxy glue, photo-curable resins, SU8, etc. can be used. The PDMS layer 308 may be about 50 μm thick, or can vary from about 10 micron to about 100 micron thick. The spin coating process may further comprise maintaining the PDMS layer 308 at about 70° C. for about 10 minutes to about 12 minutes. This temperature treatment makes the spin coated PDMS layer 308 more viscous and prevents the coating from flowing, for example. The treated PMMA sheet may be pressed against the photoresist open channel pattern with the PDMS layer 308 acting as an adhesive, as shown in FIG. 3F. The resulting microfluidic structure may be maintained at about 70° C. for about an hour to cure the PDMS layer.

Figure 4:
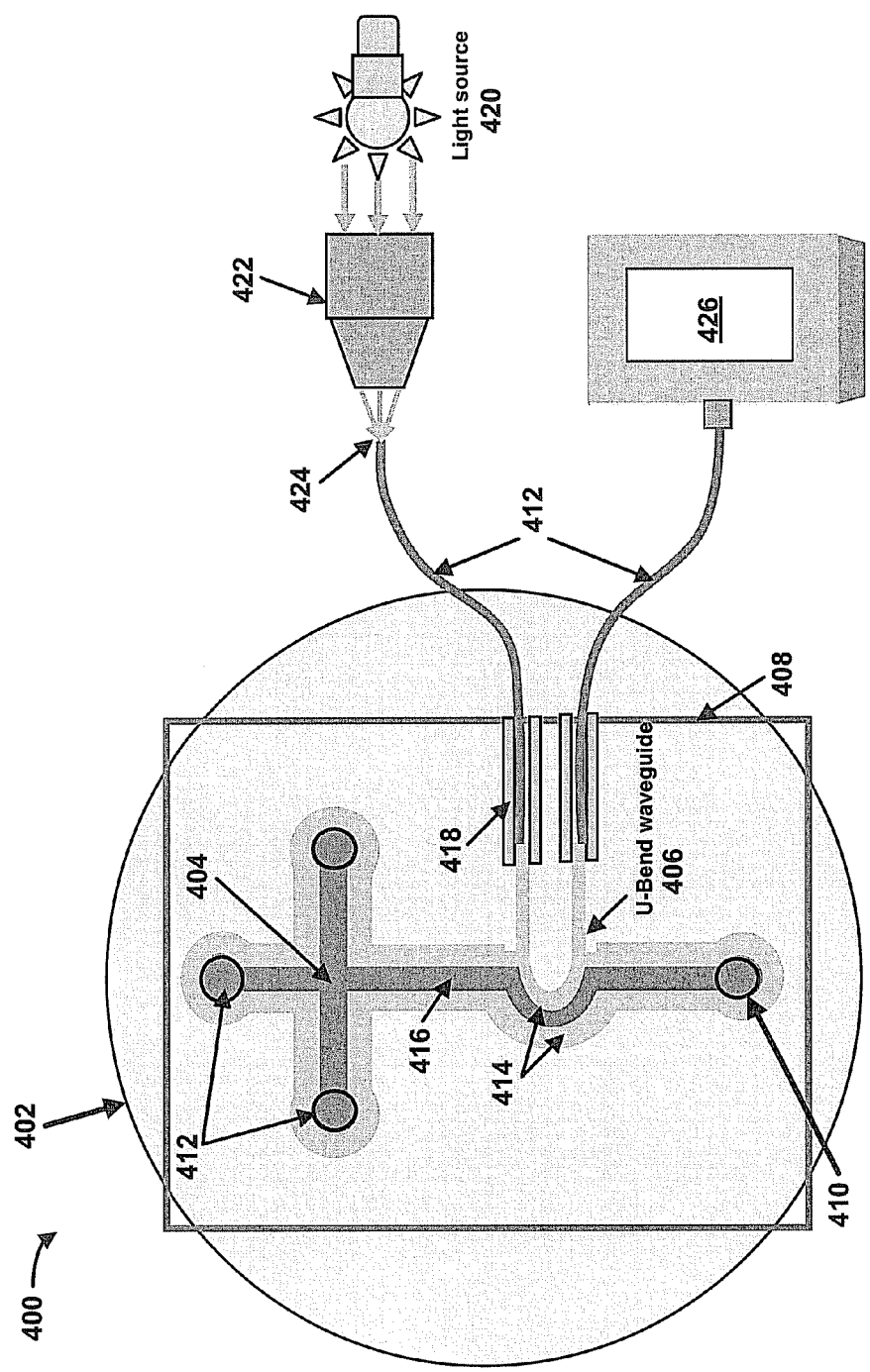
FIG. 4 illustrates a top view of a microfluidic structure fabricated using the methods described in FIGS. 3A-3F.

FIG. 4 illustrates a top view of a microfluidic structure 400 fabricated using the methods described in FIG. 3. The microfluidic structure 400 includes a silicon substrate 402 onto which microchannels are formed, such as microchannel 404. In addition, a U-bend waveguide 406 is formed on a surface the silicon substrate 402. A sheet of material 408 is pressed onto the silicon substrate and includes holes, such as holes 410 and 412, for reservoirs. The microchannel 404 has sidewalls 414 that define the microchannel, and one of the sidewalls 414 is a wall of the U-bend waveguide 406. Analyte within the microchannel 404, such as shown in the area indicated by arrow 416, flows through the microchannel 404. Optical fibers 412 may be connected to the U-bend waveguide 406 and used to deliver and collect light, for example. The optical fibers 412 may be connected to the U-bend waveguide 406 via fiber to waveguide couplers 418.

In use, for example, a light source 420 may provide light to one end of the U-bend waveguide 406 through an objective lens 422 that includes a focal point 424 of the lens to focus light into the optical fibers 418. Any other lens including a microscopic objective lens can be used to focus light from the light source 420 to a focal point where a tip of the optical fiber 412 can be placed to couple the light to an end of the U-bend waveguide 406. For example, a microscopic objective lens such as a 40×, 0.6 NA can be used to focus light from a white LED onto an end of the fiber. A detector 426, such as but not limited to a spectrometer, may be connected to the optical fibers 412 to detect light at the other end of the U-bend waveguide 406, for example. Light can be collected at the detector 426 using a variety of software packages, such as the Spectrasuite® software, to acquire absorbance spectra and real time absorbance changes at a particular wavelength, for example.

A specific example of a light source 420 may be a white LED of about 1 watt (e.g., LED 5W4HCA-H20-ULTRA, 19.0-25.0 cd at 20 mA, view angle 20°, 5 mm clear epoxy from Roithner LaserTech-nik, Austria) with a spectral emission between about 430 nm and about 700 nm. The detector 426 may be a spectrophotometer. In one specific example, the detector 426 may be a spectrophotometer such as the Ocean Optics Model, USB4000.

The microfluidic device 200 in FIG. 2A or the microfluidic device 400 in FIG. 4 may be used to analyze samples using evanescent sensing. Experiments of evanescent sensing of such devices were performed to identify evanescent field absorption and refractive index variation based changes in output power.

Figure 5:
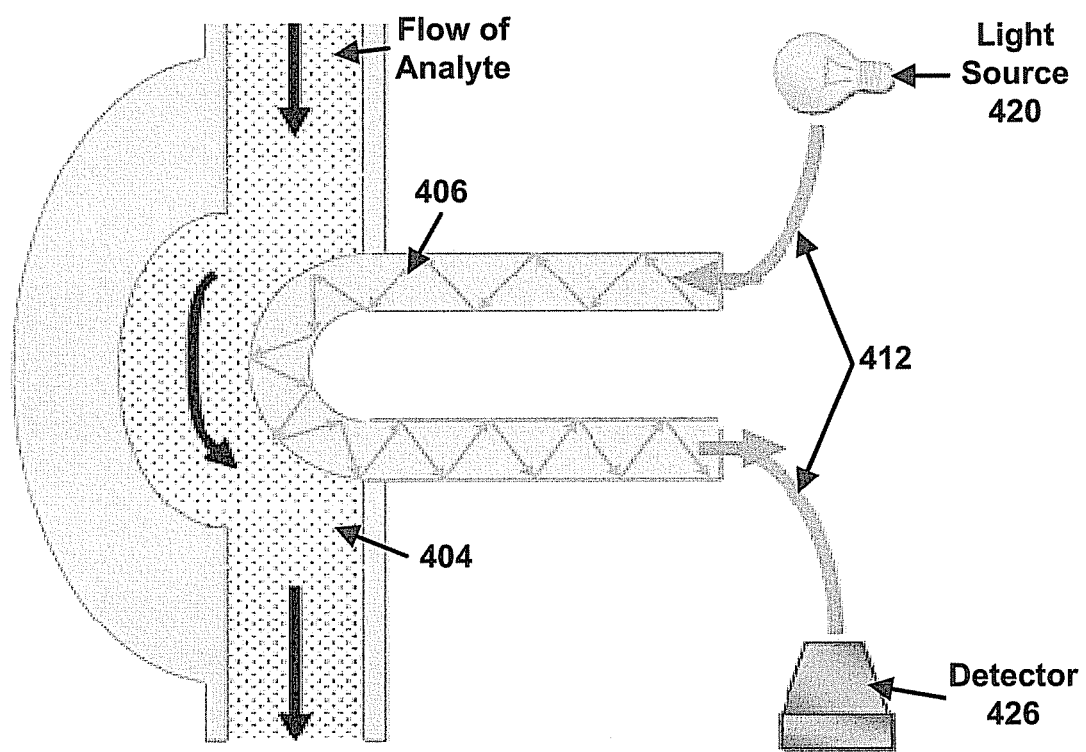
FIG. 5 illustrates an example experimental setup using the microfluidic device of FIG. 4.

FIG. 5 illustrates a magnified view of the microchannel 404 and U-bend waveguide 406 interaction. Light from the light source 420 reflects of off interior walls of the U-bend waveguide 406 and an evanescent field of the light is absorbed by analytes (shown by thick arrows) in the solution of the microchannel 404. Light that is not absorbed can be collected or detected at the detector 426.

The evanescent wave absorption by fluids present in microchannels of the microfluidic device 400 was confirmed using experiments to perform absorption measurements of Methylene Blue solutions. A detection sensitivity of Methylene Blue dye was found to be a minimum of about 0.2 μM to about 10

μM, and a sensitivity of the U-bend waveguide 406 with respect to refractive index changes in the microenvironment of the microfluidic device 400 was determined to respond to a change of about 0.0002 units to about 0.00028 units in refractive index, for example, as described below.

For measurements of evanescent wave absorbance, water was taken as a reference, and then different concentrations of dye solution were pumped into a 500×150 μm microchannel 404 to take corresponding readings. Before each concentration was introduced into the microchannel 404, an air bubble was first injected into the microchannel 404 to separate the solutions, and to lessen or eliminate error caused by mixing of two different successive concentrations.

Figure 6:
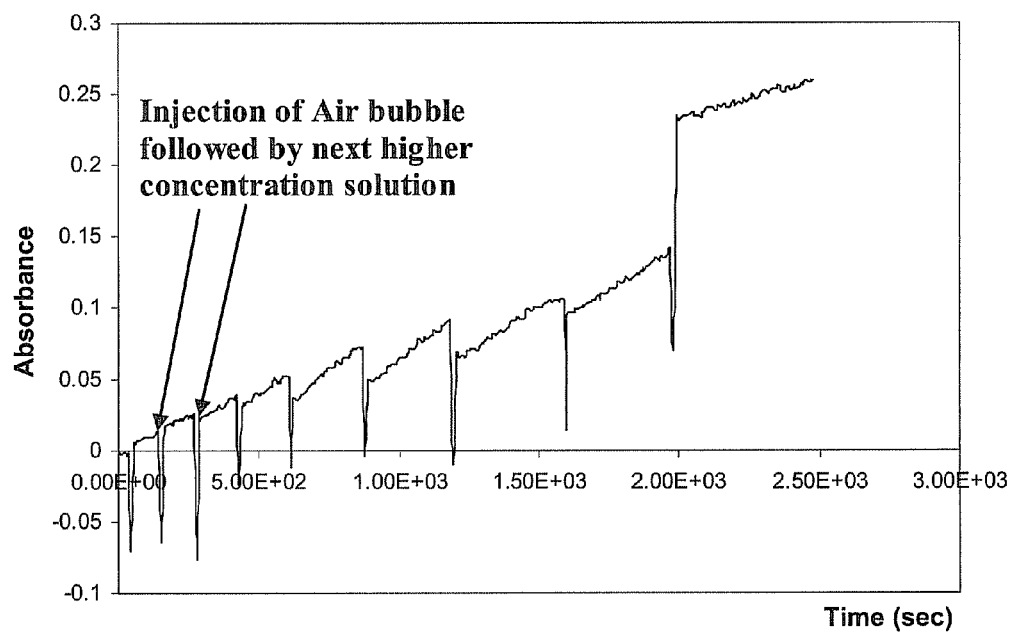
FIG. 6 is a graph that illustrates example measurements of absorption of light over time by different concentrations of Methylene blue using the microfluidic device of FIG. 2A.

FIG. 6 is a graph that illustrates example measurements of absorption of light over time by different concentrations of Methylene blue. Injection of the air bubble causes a sudden steep decrease in absorbance which is shown in the graph in FIG. 6. The next higher concentration dye solution injected after the air bubble causes a sudden steep increase followed by a gradual increase in absorbance. The gradual increase may be due to absorption of Methylene blue onto the waveguide, for example.

Figure 7:
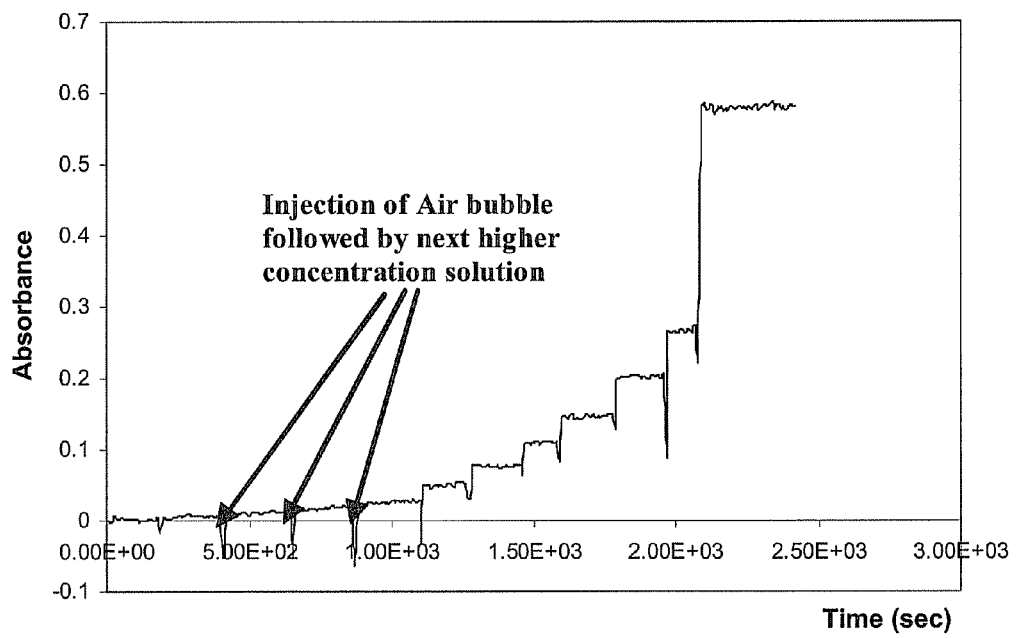
FIG. 7 is a graph that illustrates example measurements of absorption of light over time by different concentrations of sucrose solution (having different refractive indexes) using the microfluidic device of FIG. 2A.

FIG. 7 is a graph that illustrates example measurements of absorption of light over time by different concentrations of sucrose solution (having different refractive indexes). Injection of the air bubble causes a sudden steep decrease in absorbance which is shown in the graph in FIG. 7. The next higher concentration dye solution injected after the air bubble causes a sudden steep increase followed by a gradual plateau.

Figure 8:
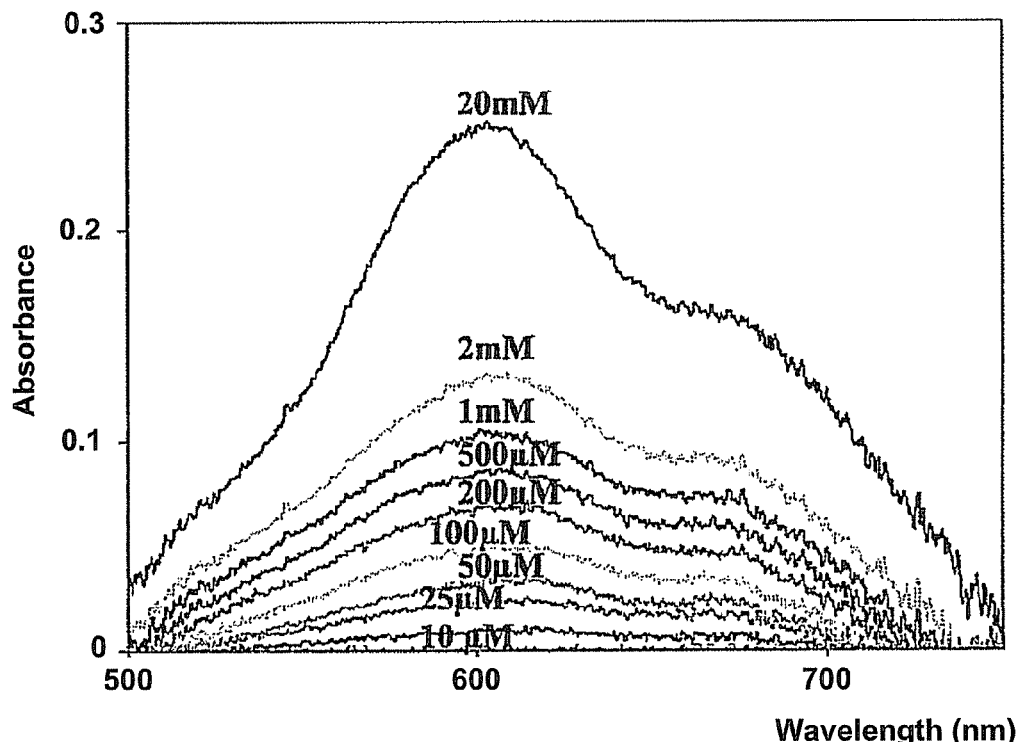
FIG. 8 is an example graph of the absorption spectra of different Methylene blue concentrations using the microfluidic device of FIG. 2A.

After each set of measurements for different dye solutions, the microchannel 404 was flushed with deionized water and an absorption spectrum was obtained. For example experimental observations, absorbance of deionized water filled in the micro-channel was taken as a reference or background value (i.e., zero absorbance). FIG. 8 is an example graph of the absorption spectra of the different Methylene blue concentrations. Absorbance is defined as shown above in Equation (5), and thus, has no units, or alternatively, may be considered to have "Absorbance Units" or AU.

Water absorption is equivalent to the zero line in FIG. 8. A detection limit of Methylene Blue solution for a waveguide detection length with the experimental setup was found to be about 10 μM.

Figure 9:
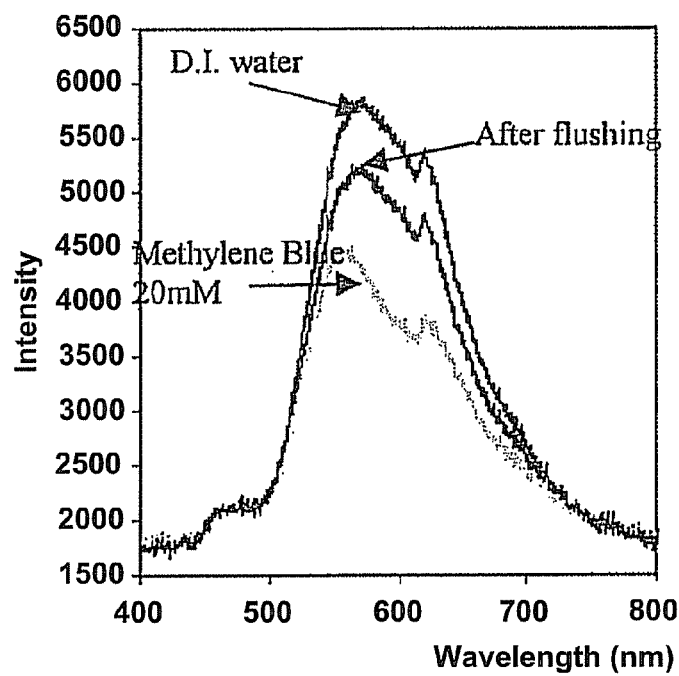
FIG. 9 is an example graph of intensity versus wavelength of deionized water, 20 mM Methylene blue, and after flushing the 20 mM Methylene blue microchannel with deionized water using the microfluidic device of FIG. 2A.

FIG. 9 is an example graph of intensity versus wavelength of deionized water, 20 mM Methylene blue, and after flushing the 20 mM Methylene blue microchannel with deionized water. Measurements of light are generally measurements of light intensity, which can be obtained by dividing either a power or a luminous flux by a solid angle, a planar area, or a combination of the two, for example. As one example, a radiometric measurement may include an angular measurement that is a measurement of radiant intensity measured in watt per steradian (W/sr), or an areal measurement that is a measurement of irradiance measured in watts per square meter. As another example, a photometric measurement may include an angular measurement that is a luminous intensity measured in lumens per steradian (lm/sr) or candela (cd), or an areal measurement that is measured in lumens per square meter or lux (lx) (illuminance is for light incident on a surface, and luminous emittance or luminous exitance is for light emitted from a source).

Figure 10:
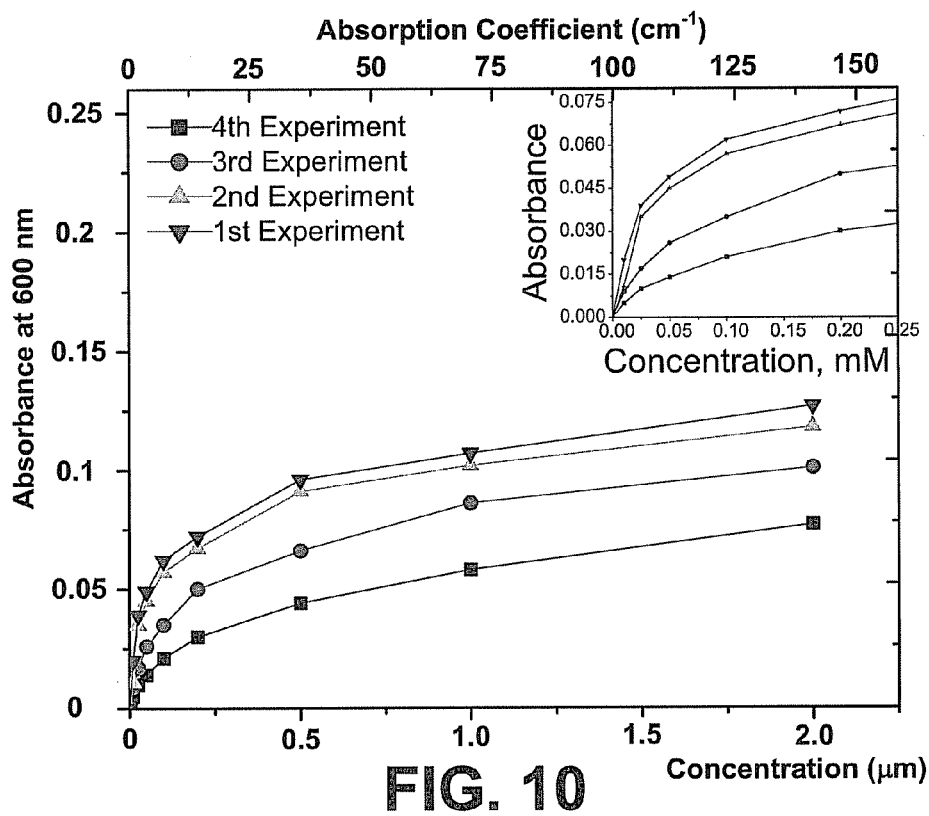
FIG. 10 is a graph that illustrates an example calibration curve for Methylene Blue using measurements made with the microfluidic device of FIG. 2A.

FIG. 10 is a graph that illustrates an example calibration curve for Methylene Blue (MB) at 600 nm, and an inset graph illustrating a calibration curve of Methylene Blue at 600 nm below 500 μm concentration. As shown in FIG. 10, an initial rise in absorbance gives way to a slower rise at higher concentrations. This may be attributed to a comparatively higher rate of absorption due to lower stearic on the surface at lower concentrations. For example, at lower concentrations, the adsorption values may be smaller so that a greater relative change in absorbance will be observed with a concentration change; at higher concentrations more of the surface of the waveguide may be occupied by adsorbed MB molecules and there may be smaller interactions to the evanescent field with a higher number of introduced MB molecules. Thus, a smaller response of absorbance change may occur with increasing concentration.

MB molecules are used as an example to demonstrate evanescent field absorption of the device. Because of the MB molecules positively charged nature, they bind and absorb to negatively charged SU8 surfaces and provide a non-linear response at higher concentrations. Other molecules may provide linear responses if the molecules do not absorb to the SU8 surfaces. In one example, to lessen or prevent MB absorption on the SU8 surfaces, the SU8 surface of the waveguide can be coated with a positively charged or neutral polymer layer to inhibit binding.

FIG. 10 also depicts a decrease in sensitivity as experiments are repeated on the same waveguide. Flushing and cleaning the waveguide after experiments may improve sensitivity, for example. Experiments performed with microchannels of varying widths did not yield significantly different results because the evanescent wave penetration depth is in the range of about a few microns. Channel widths of 150 μm, 200 μm, and 500 μm were tested.

Figure 11:
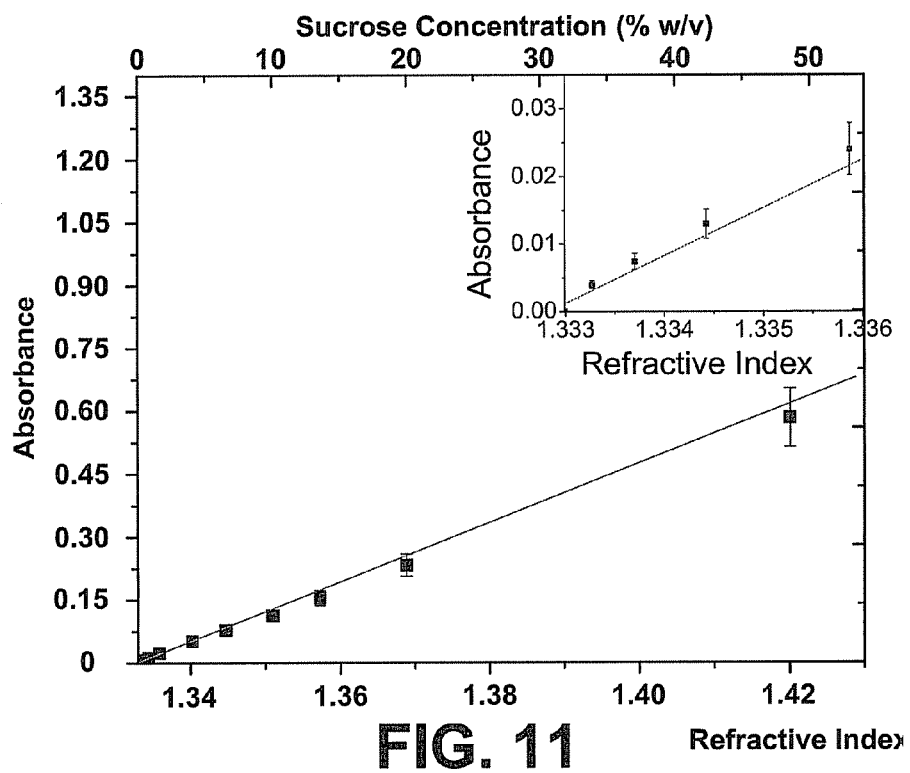
FIG. 11 is an example graph of changes in absorbance with changes in refractive indices of the external medium using the microfluidic device of FIG. 2A.

For measurements of refractive index variation based changes in absorbance and output power, sucrose solutions with different refractive indices (due to varying concentrations) were passed through the microchannel 404 while measurements were taken. FIG. 11 is an example graph of changes in absorbance with changes in refractive indexes of the external medium, and includes an inset graph illustrating a calibration curve of MB at 600 nm below 500 μm concentration. The results illustrate that sensitivity depends on the refractive index of the external medium. The absorbance results from a change in lost refracted light rays away from the waveguide 406 and is proportional to a change the refractive index of the external medium. The waveguides fabricated in these experiments were sensitive to changes of about 0.00028 units in refractive index of the medium flowing in the microchannel 404, for example. The absorbance measurement gives a change in light intensity output of the waveguide as compared to a reference solution. The device can be used for portable sensor applications for sensing refractive index of a solution, sensing concentration of optically absorptive (bio) chemical compounds, detection in capillary electrophoresis, as well as various lab on chip bio-sensing or bio-mems applications.

Figure 12:
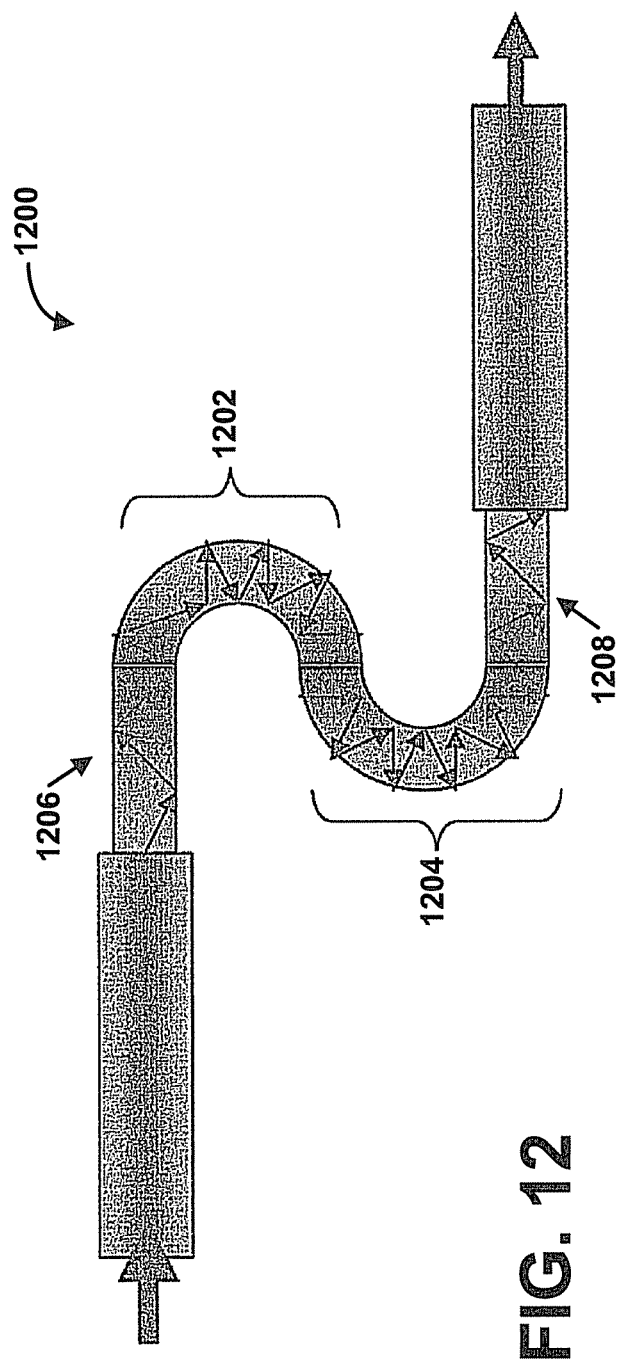
FIG. 12 illustrates an example S-bend waveguide.

In other embodiments, the waveguide may be configured in alternate shapes, or multiple U-bend shapes may be used. For example, as shown in FIG. 12, a waveguide for a microfluidic device may be configured as an S-bend waveguide 1200, which may comprise multiple U-bend waveguides 1202 and 1204. The S-bend waveguide has two U-bend structures in the design interfacing to the microchannels, and thus, the S-bend waveguide may enhance performance of the device. Further, the S-bend waveguide may utilize both inner and outer bend surfaces of the waveguide interfacing to the microchannels, which further increases sensitivity (e.g., up to four times as much as a single U-bend waveguide). Overall length of a straight section of the waveguide interfacing to the microchannels is about three times as long as a single U-bend waveguide. An overall sensitivity of the S-bend waveguide is about ten times than of the single U-bend waveguide, for example. The U-bend waveguides 1202 and 1204 each may operate as described above with respect to FIG. 1, for example. Although FIG. 12 illustrates two U-bend waveguides in an S-bend configuration, more U-bend waveguides may be used to form still further configurations.

Similar to the U-bend waveguide 100 in FIG. 1, the S-bend waveguide 1200 includes a first substantially linear section 1206 that connects to the U-bend waveguide 1202. A second substantially linear section 1208 connects to the U-bend waveguide 1202 via the U-bend waveguide 1204. An optical beam of light is received at the first linear section 1206 and is guided through the U-bend waveguides 1202 and 1204 to the second linear section 1208.

Each of the U-bend waveguides 1202 and 1204 may be semi-circle sections configured as a U-shape, for example, and may have an arc or curvature about 180°. These semi-circle sections may be configured as half of a circle, for example, and may be configured to curve inward or outward depending on a configuration of the S-bend waveguide 1200. For example, the U-bend waveguide 1202 curves in a first direction, and the U-bend waveguide 1204 curves in a second direction that is opposite the first direction. The U-bend waveguide 1202 may be considered to be convex and the U-bend waveguide 1204 may be considered to be concave, for example. Together, the U-bend waveguides 1202 and 1204 form an S-shape, for example, and may be configured to be a forward or reverse S-shape. FIG. 12 illustrates the S-bend waveguide 1200 to be in a reverse S-shape, for example.

Portions of the S-bend waveguide 1200 (e.g., such as any of the first linear section 1206, the U-bend waveguides 1202 and 1204, or the second linear section 1208) may have a width of about 200 μm, for example, and the U-bend waveguides 1202 and 1204 may have a curvature diameter of about 1 mm.

FIGS. 13A-D illustrate example mask designs of a microfluidic device that comprise S-shaped waveguides. For example, FIG. 13A illustrates a microfluidic device 1300 that comprises an S-bend waveguide 1302 coupled to a source waveguide 1304 and a detector waveguide 1306. The S-bend waveguide 1302 may be about 200 μm thick, and the source waveguide 1304 and detector waveguide 1306 may be about 400 μm thick, for example.

The S-bend waveguide 1302 has sidewalls (e.g., side wall 1308) that forms a portion of the microchannels 1310. The microchannel 1310 may be about 300 μm thick, or in the range of about 100 μm to about 500 μm thick. The microchannels 1310 are connected to an inlet reservoir 1312 and an outlet reservoir 1314 into which a sample may be inserted and output.

To couple light into the S-bend waveguide 1302, fiber-to-waveguide coupler structures 1316 and 1318 are used. The fiber-to-waveguide coupler structure 1318 couples an LED source to the S-bend waveguide 1302 through the source waveguide 1304, and the fiber-to-waveguide coupler structure 1316 couples a spectrophotometer to the S-bend waveguide 1304 through the detector waveguide 1306. The fiber-to-waveguide coupler structures 1316 and 1318 may include a tapered groove that can be inserted into the source and detector waveguides 1304 and 1306 to ensure fiber alignment with the waveguides 1304 and 1306, for example.

FIG. 13B illustrates a magnified view of the microfluidic device 1300. The S-bend waveguide 1302 comprises side by side S-bend waveguides 1322 and 1324. Each of the S-bend waveguides 1322 and 1324 are connected to the source and detector waveguides 1304 and 1306. The source waveguide 1304 connects to the S-bend waveguides 1322 and 1324 through the inlet reservoir 1312, and the detector waveguide 1306 connects to the S-bend waveguides 1322 and 1324 through the outlet reservoir 1314. The S-bend waveguides 1322 and 1324 are bifurcated waveguides, and form side walls for three separate microchannels 1334, 1336, and 1338. More microchannels and/or more S-shaped waveguides may be included, however.

FIG. 13C illustrates another example mask design of a microfluidic device 1340 that includes one S-bend waveguide 1342 connected to one microchannel. The S-bend waveguide 1342 is connected to a source waveguide 1346 through an inlet reservoir 1348, and the S-bend waveguide 1342 is connected to a detector waveguide 1350 through an outlet reservoir 1352. Each of the source waveguide 1346 and detector waveguide 1350 are connected to fiber to waveguide couplers 1352 and 1354, respectively. FIG. 13D illustrates a magnified view of the S-bend waveguide 1342, the microchannel 1344, and a microchannel side wall 1356.

Figure 13E:
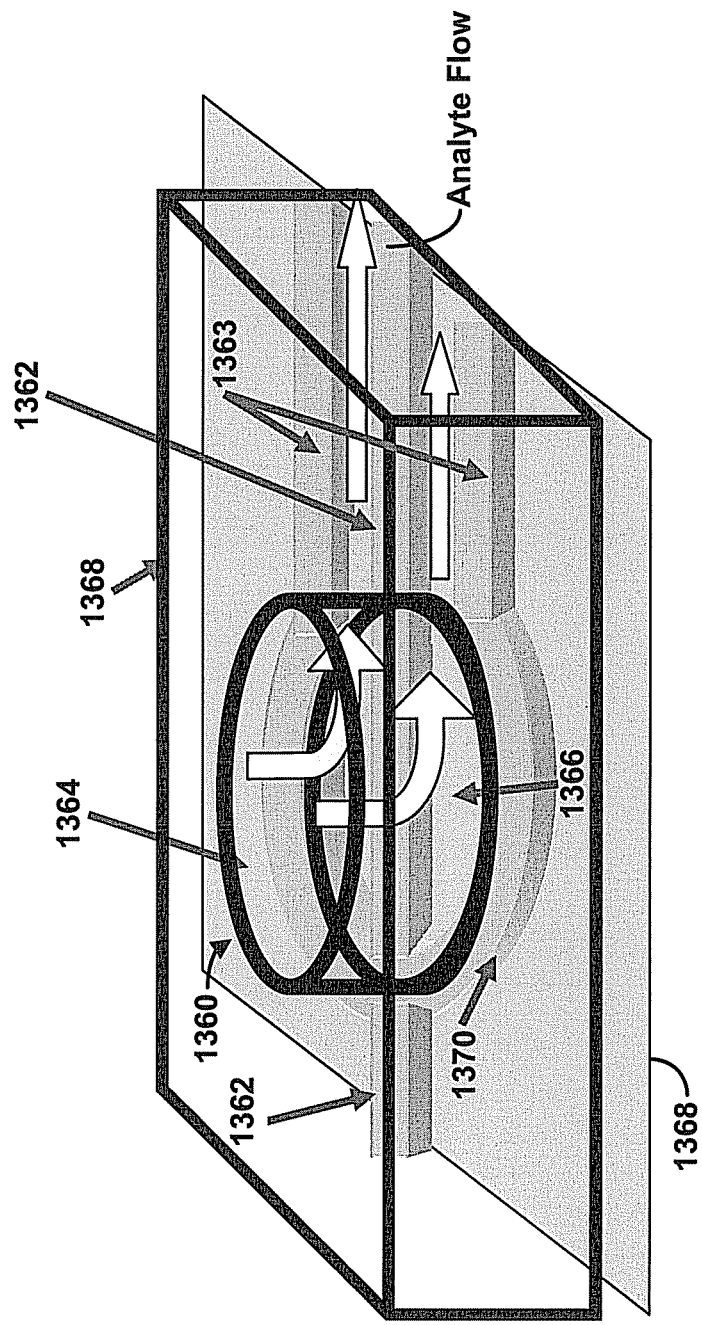

FIG. 13E illustrates an example connection of a reservoir 1360 to a waveguide 1362 and microchannels 1363. The reservoir 1360 can be divided into an upper section 1364 and lower section 1366. The lower section 1366 comprises patterned SU8 and the upper section 1364 comprises a hole created on a flat PMMA substrate 1368 bonded over an open SU8 microchannel to seal the hole. The microchannels 1362 ends into the lower section 1366 of the reservoir 1360. The reservoir 1360 may be formed on a substrate 1368 (e.g., $SiO_2$) and includes sidewalls 1370.

Thus, FIG. 13A illustrates an example microfluidics device 1300 with two S-bend waveguides and three microchannels 1310, and FIG. 13C illustrates an example microfluidic device with one S-bend waveguide and one microchannel. Any number of S-bend waveguides may be incorporated into a microfluidics device, and any resulting number of microchannels can be formed, for example.

In addition, the microfluidic devices illustrated in FIGS. 13A-C may include a combination of S-shaped waveguides, and U-bend waveguides (not shown) depending on a configuration of the microfluidic device, for example. Further, more U-bend waveguides may be included so as to form a waveguide including 3 U-bends, 4 U-bends (e.g., two S-shape waveguides), and additional multiples thereof. Any number of bends or U-bends may be included resulting in any number of S-shape waveguides, or combination of U-bend and S-shape waveguides, for example.

By including an additional U-bend waveguide to create a given S-shaped waveguide, a sensitivity of the resulting microfluidic device may be increased. As described above, in a U-bend waveguide, when light is transmitted through the U-bend, the evanescent field extends deeper into the surrounding medium at the U-bend region. If the analytes absorb light in the particular wavelength that is being used, then an intensity of light at the detector end of the waveguide decreases. Light absorbance in the U-bend region is proportional to concentration of the analytes. Referring to Equations (1)-(4) above, the sensitivity of the microfluidic device is increased because the length of interaction (L in Equations (1) and (4)) is larger due to two U-bend waveguides forming the S-shaped waveguide, and η (the fraction of light in the evanescent domain) will be larger because the waveguide is bended twice and more fraction of light will travel in evanescent mode, for example. The sensitivity may be further increased by adding more U-bends to the waveguide, for example, to increase a length of interaction.

Referring again to FIGS. 13A and 13C, the microfluidic devices may be fabricated in a manner similar to that described above with respect to FIGS. 3A-3D. For example, a single photoresist process may be used to define both optical and fluidic structures of the microfluidic device.

The microfluidic device in any of FIGS. 13A and 13C exploits interaction between the evanescent field penetrating into the absorbing medium. The wavelength of light can be selected according to a peak absorption wavelength of the absorbing fluid. This leads to the loss of transmitted power due to absorption of the evanescent wave penetrating into the absorbing medium. The measured optical attenuation along the waveguide is used to determine a concentration and refractive index of the absorbing fluid, for example.

For a given length of the unclad fiber (e.g., waveguide), the sensitivity or evanescent wave absorption relies upon a number of ray reflections per unit length and penetration depth of the evanescent field in the sensing region of the waveguide. Fluid in which samples are placed for experiments can be chosen so that the fluid will have negligible evanescent field absorption properties with cladding material of the waveguide.

The microfluidic devices in any of FIGS. 13A-C may be used to analyze samples using evanescent sensing. For example, the detector waveguide 1306 may detect changes in an evanescent field or refracting index of a sample liquid in the microchannels 1310 (resulting from concentration changes). Experiments of evanescent sensing of such devices were performed to identify evanescent field absorption and refractive index variation based changes in output power.

To perform the experiments, a red LED of about 1 watt power was used as a light source and a spectrophotometer was used as a detector. Suitability of this light source and detector for analytical purposes was demonstrated by evanescent wave absorption measurements on Methylene Blue solution and antigen antibody interaction using optical fibers (described below). Methylene Blue exhibits maximum absorbance at 575-625 nm, for example.

The evanescent wave absorption by fluids present in the microchannels 1310 was confirmed using experiments to perform absorption measurements of Methylene Blue solutions. A detection sensitivity of Methylene Blue dye was found to be about 0.2 μM, and a sensitivity of the S-bend waveguide 1302 with respect to refractive index changes in the microenvironment of the microfluidic device 1300 was determined to respond to a change of about 0.0002 units in refractive index. For evanescent wave detection based sensing, the sensitivity may be about 10 times higher than the sensitivity of the single U-bend waveguide microfluidic device, for example.

For measurements of evanescent wave absorbance, water was taken as a reference and then different concentrations of dye solution were inserted into the S-bend microchannels 1310 (each of width of about 200 μm to about 300 μm) to take corresponding readings.

Figure 14:
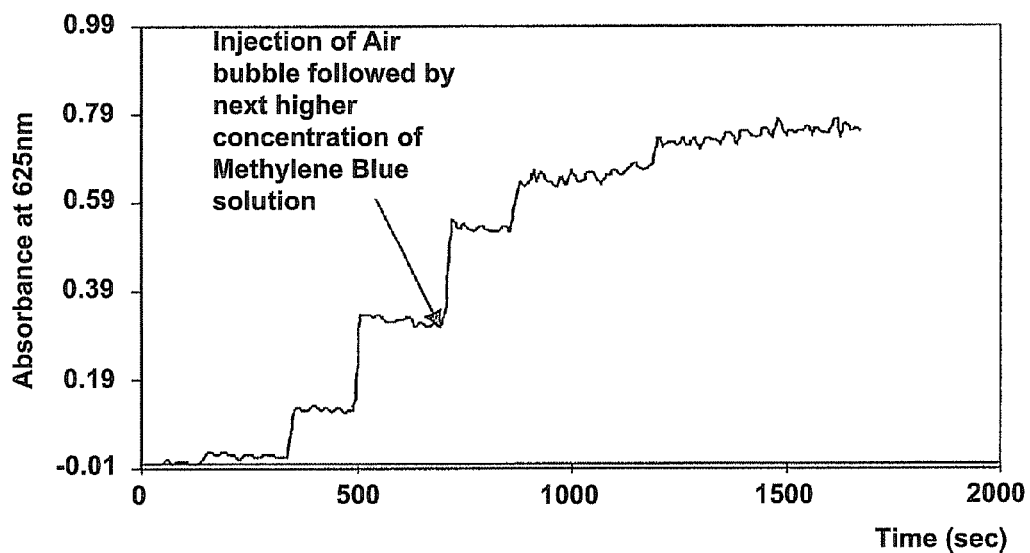
FIG. 14 is a graph that illustrates example measurements of absorption of light over time by different concentrations of Methylene blue using the microfluidic device of FIG. 13.

FIG. 14 is a graph that illustrates example measurements of absorption of light over time by different concentrations of Methylene blue. Injection of the air bubble causes a sudden steep decrease in absorbance which is shown in the graph in FIG. 14. The next higher concentration dye solution injected after the air bubble causes a sudden steep increase.

Figure 15:
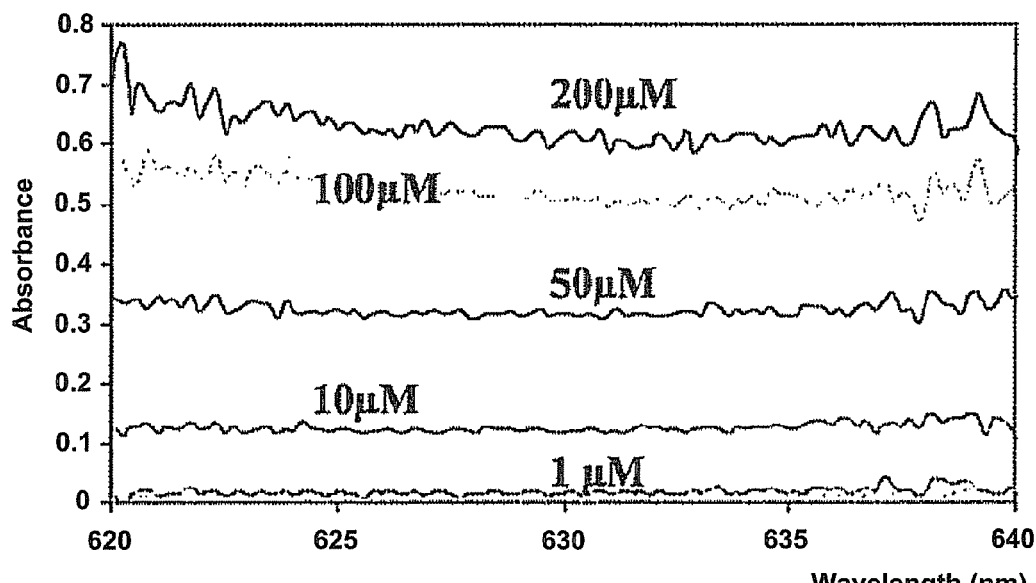
FIG. 15 is an example graph illustrating the absorption spectra of different Methylene blue concentrations using the microfluidic device of FIG. 13.

After each set of measurements for different dye solutions, the microchannels were flushed with deionized water and absorption spectrum was obtained. FIG. 15 is an example graph illustrating the absorption spectra of different Methylene blue concentrations (e.g., 1 μM, 10 μM, 50 μM, 100 μM, and 200 μM). Water absorption is equivalent to the zero line in FIG. 15.

Figure 16:
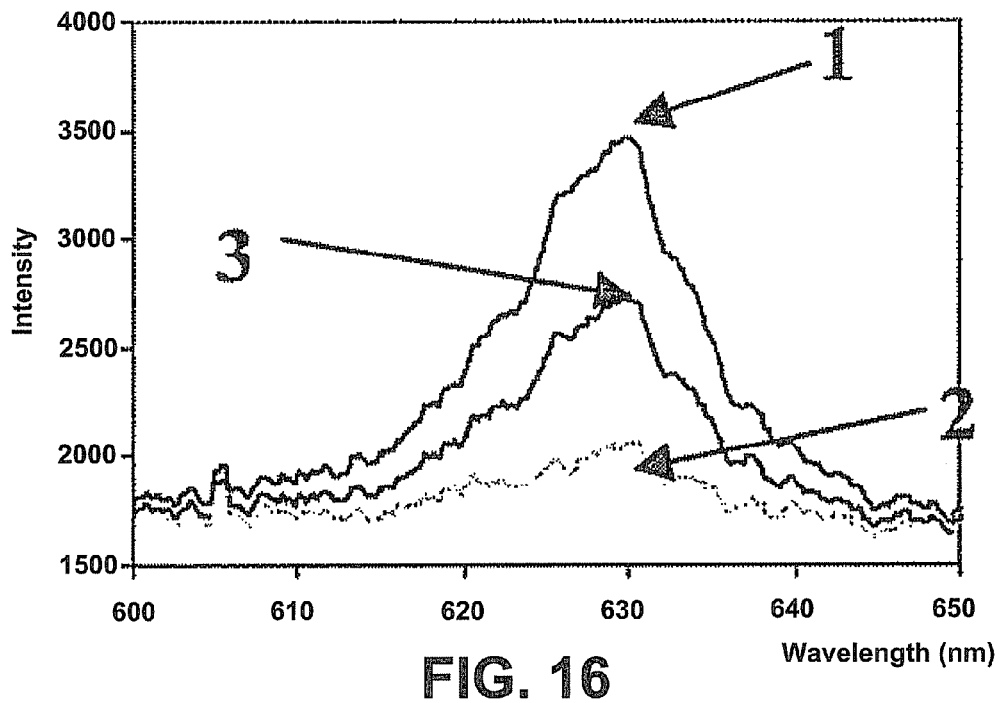
FIG. 16 is an example graph that illustrates intensity versus wavelength of deionized water (1), 1 mM Methylene blue (2), and after flushing 1 mM Methylene blue filled microchannel with deionized water (3) using the microfluidic device of FIG. 13.

FIG. 16 is an example graph that illustrates intensity versus wavelength of deionized water (1), 1 mM Methylene blue (2), and after flushing 1 mM Methylene blue filled microchannel with deionized water (3). Initially, the three S-shaped microchannels integrated within the two S-shaped waveguides were filled with water and dark and light references were taken, as shown by the line labeled (1). Afterwards, the microchannels were filled with 1 mM concentration of Methylene blue and the intensity versus wavelength graph were obtained, as shown by the line labeled (2). The Methylene blue dye filled channel was flushed with deionized water and the intensity versus wavelength graph as shown by the line labeled (3) was obtained. A comparison of the spectrum labeled (3) with the spectrum taken before the injection of dye and that taken with 1 mM dye shows that there is some residual absorption at the end, which may be due to adsorption of Methylene blue on the waveguide surface, for example.

A detection limit of a Methylene Blue solution for a microfluidic device as shown in FIG. 13 was found to be about 0.2 μM.

Figure 17:
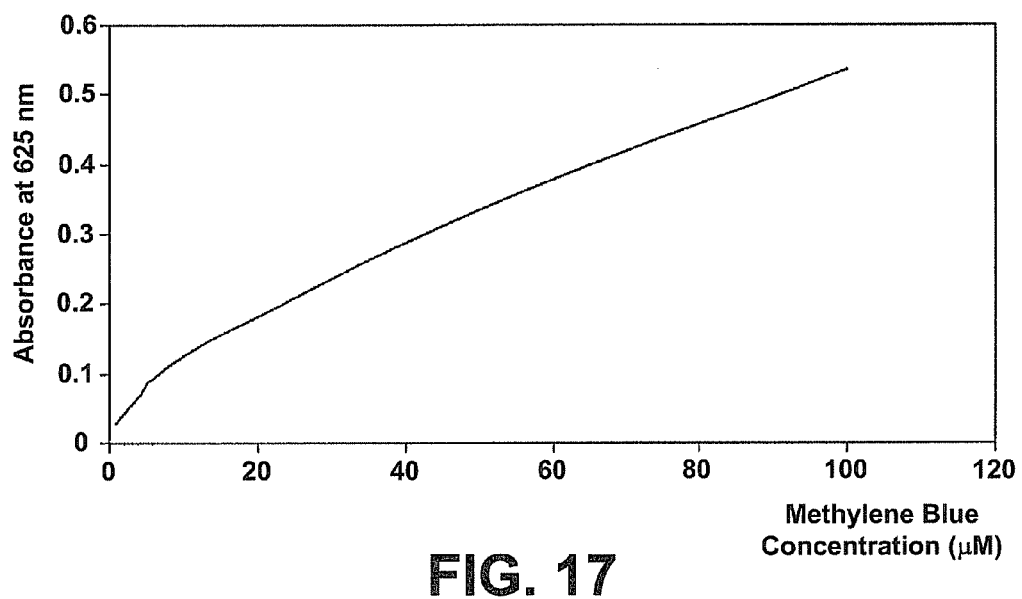
FIG. 17 is a graph that illustrates a calibration curve for Methylene Blue using measurements made using the microfluidic device of FIG. 13.

FIG. 17 is a graph that illustrates a calibration curve for Methylene Blue at 625 nm. As shown in FIG. 17, an initial quick rise in absorbance gives way to a somewhat slower rise at higher concentrations. This may be attributed to a comparatively higher rate of adsorption due to lower stearic on the surface at lower concentrations.

Any of the microfluidic devices described herein may be used as a biosensor, for example. Biosensing may be accomplished, for example, using Human IgG (HIgG)-FITC tagged goat anti IgG(GaHIgG) biomolecules as bioreceptor-analyte pairs. In one example, for HIgG immobilization on a waveguide, glycine was used as crosslinkers before applying carbodiimide/succinimide chemistry over a surface of the waveguide. The analyte (FITC tagged GaHIgG) was passed through the micro-channel embedded with the waveguide. Antigen-antibody interaction and binding results in absorption of an evanescent field by FITC tagged GaHIgG biomolecules, causing a decrease in light intensity output of the waveguide that can be detected and calibrated. Results indicated that U-shaped waveguides can be used for bio sensing of biomolecules either by evanescent wave absorption or by detecting changes associated with refractive index changes in the microenvironment around a waveguide, for example.

For bio-receptor immobilization on a surface of the waveguide, modifications to the waveguide can be made. For example, a surface of the waveguide after UV exposure may have a larger number of epoxy groups as compared to hydroxyl groups. Thus, an increment in the number of surface hydroxyl groups may be required for a successful HIgG immobilization procedure. For this reason, a surface of the waveguide can be treated with 0.1 M NaOH for about 10 minutes and 1 M HCl for about 10 minutes by introducing these solutions into the embedded microchannel. Next, a surface of the waveguide may be treated with 5 mM glycine in aqueous solution for about 2 hours. Due to availability of hydroxyl groups on the surface of the waveguide, amines of glycine molecules may bind to the surface through hydrogen bonding and electrostatic attractions. The embedded microchannel may then be flushed with deionized water after 2 hours and the surface of the waveguide may be activated with EDC:NHS (0.2 M:0.1 M in deionized water) for about 1 hour. Human Immunoglobin G (HIgG) may be covalently immobilized to carboxylic acid on the surface using this carbodiimide/succinimide chemistry.

Figure 18:
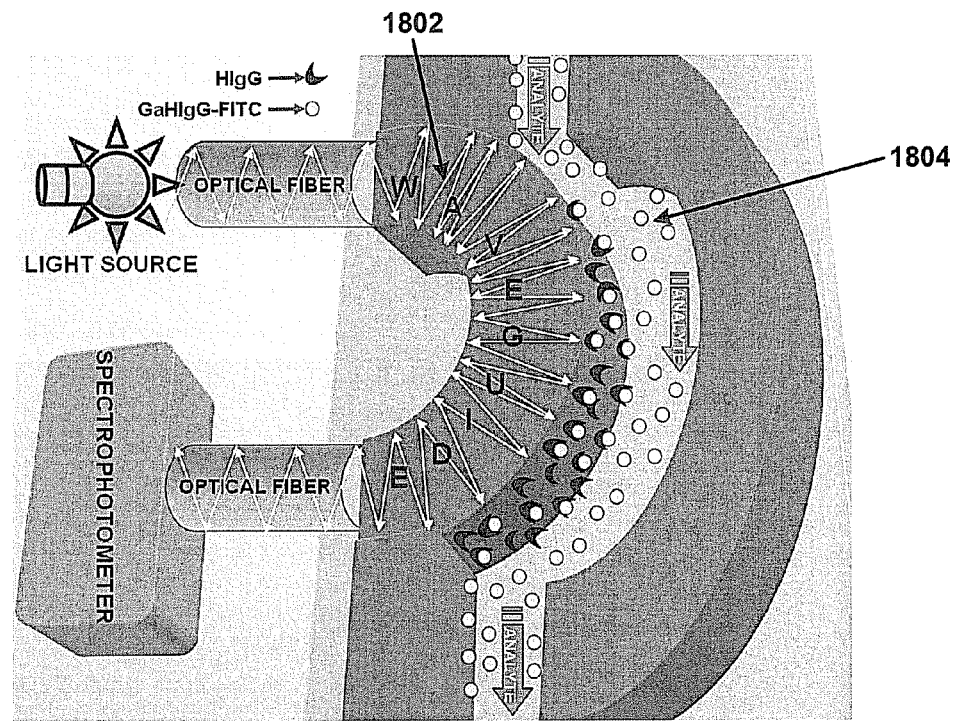
FIG. 18 is an example optical set-up that may be used for biosensing.

FIG. 18 is an example optical set-up that may be used for biosensing. As shown, a U-bend waveguide 1802 may be treated with HIgG, and the analyte may be passed through a microchannel 1804 and allow to react with the HIgG treated surface. The human IgG (HIgG) solution of 0.1 mg/ml concentration may be prepared in PBS and incubated with succinimide activated substrates overnight at about 4° C. The embedded microchannel 1804 may be flushed about 5-6 times with PBS to remove loosely adsorbed HIgG biomolecules. The surfaces of the waveguide 1802 may be treated with 1 mg/ml BSA solution in PBS to block non-specific binding sites of HIgG, for example.

In example experiments, absorbance changes over time for a particular wavelength were calculated from acquired data. A signal-to-noise ratio (SNR) was improved by averaging 50 consecutive spectra. The waveguide 1802 was initially tested for RI sensitivity, and evanescent absorbance at the U-shaped waveguide 1802 interfacing the deionized water was taken as a background signal. Evanescent absorbance of various higher RI solutions from about 1.33 to about 1.37 was observed with respect to the same background. Example absorbance values for the waveguide 1802 at 589 nm for different refractive indices are shown in the graph illustrated in FIG. 19. Sensitivity, defined as a ratio of a change in absorbance to a change in RI, was found to be relatively linear between about 1.33 and about 1.37 RIU, and had a value of approximately 2.5 $A_{530nm}$/RIU for the probe.

Figure 19:
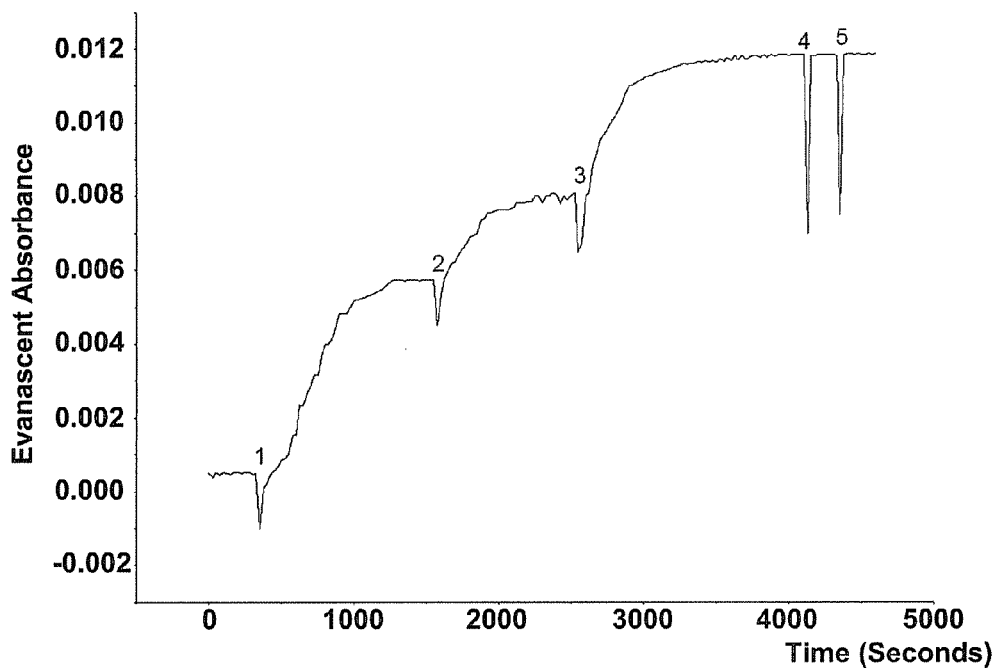
FIG. 19 illustrates a graph of changes in absorbance recorded from a HIgG immobilized embedded U-shaped waveguide probe.

FIG. 19 thus illustrates a graph of changes in absorbance recorded from a HIgG immobilized embedded U-shaped waveguide probe (as shown in FIG. 18) when subjected to (1) 13 µg/mL; (2) 25 µg/mL and (3) 50 µg/mL GaHIgG-FITC solution (by introducing corresponding GaHIgG-FITC solution into microchannel 1804 followed by an air bubble) until saturation is obtained (or approximately obtained). A volume of biomolecules needed may depend upon a volume of the microchannel and reservoir to be filled, and may be in a range of microliters. Further, to detect less than about 13 µg/mL, a device with higher analyte surface area of interface with the waveguide can be used (e.g., the S-bend device). The microchannel 1804 was flushed with a buffer for two times at 4, 5 on the graph to flush out remaining antigen solution. To remove bound antigens, the waveguide can be flushed with 10 mM NaOH solution for about 30 minutes, for example.

For biosensing of a particular analyte molecule, an outer periphery of the U-shaped waveguide 1802 can be immobilized with a complementary bio-receptor molecule. This immobilization may cause an increase in a refractive index in the microenvironment of the waveguide 1802 that leads to an increase in an optical absorbance of the waveguide 1802. Interaction of target analyte molecules with bioreceptor molecules may cause further increases in refractive index in the microenvironment of an outer periphery of the waveguide 1802 that may lead to a further increase in the optical absorbance of the waveguide. Thus, a change in optical absorbance through the waveguide 1802 may prove the presence of a target analyte molecule, for example.

As another example of using the U-shaped waveguide 1802 for biosensing applications, a bioreceptor-analyte pair of IgG-anti IgG was used in an experiment. The waveguide 1802 was immobilized with bio-receptor (HIgG) molecules as described above. HIgG immobilized probes were used with different concentrations of FITC tagged GaHIgG ranging between about 13 µg/mL and about 50 µg/mL. To separate each of consecutively introduced higher concentration GaHIgG solutions, a micron size air bubble was injected between solutions. A sudden decrease in absorbance prior to each higher concentration GaHIgG-FITC solution introduction resulted due to the introduced air bubble. The microchannel 1804 was flushed 2 times with buffer solution at an end of the experiment to measure a final change in absorbance. The saturated absorbance response due to binding of GaHIgG to immobilized HIgG was about 0.012. The absorbance response was observed for about 1.5 hours, and the microfluidics device detected a concentration of about 13 µg/ml of the analyte, for example.

Figure 20:
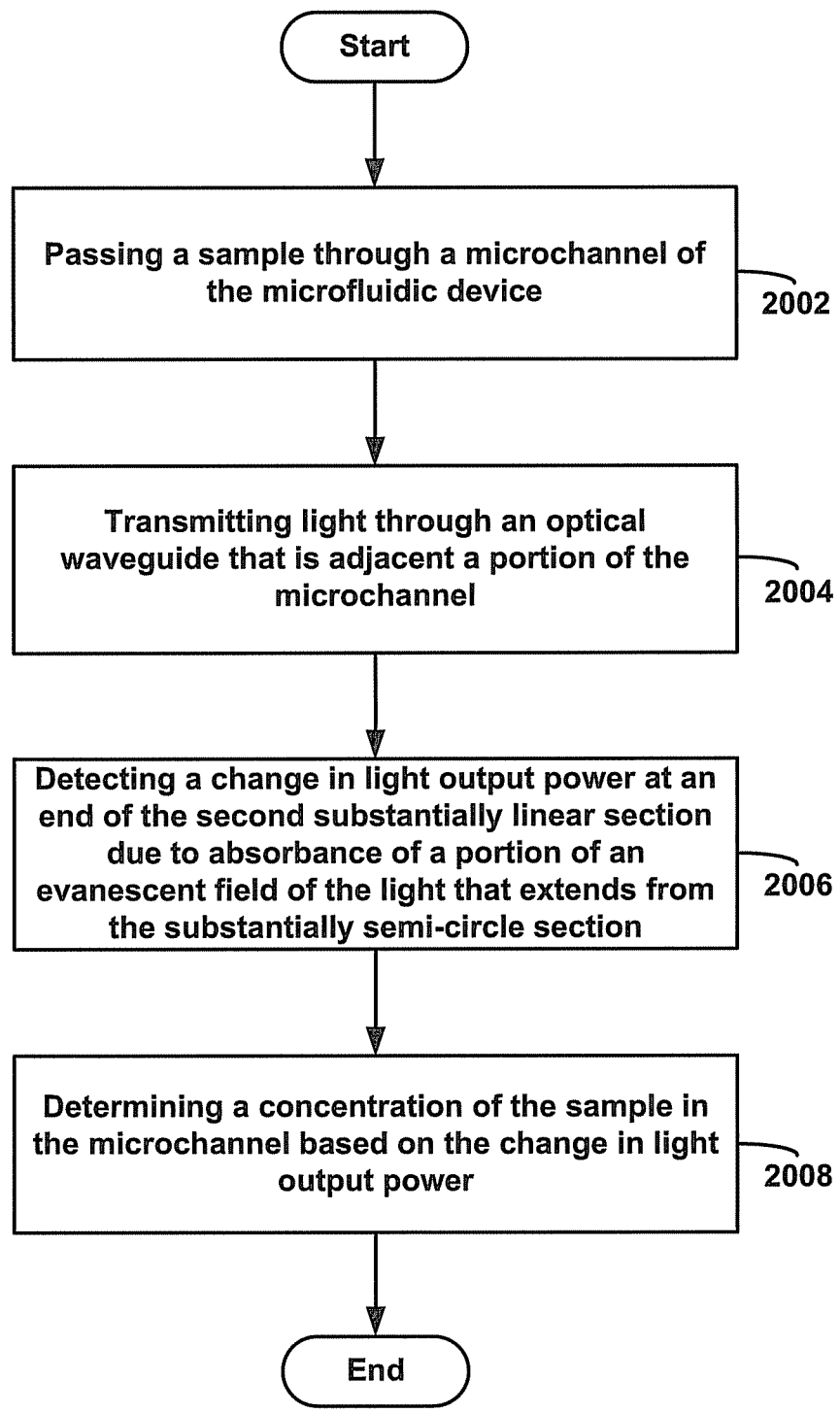
FIG. 20 shows a flowchart of an illustrative embodiment of a method for detecting an analyte or a concentration of a solution in a microchannel of a microfluidic device.

Any of the example microfluidic devices described herein may be used to detect an analyte or a concentration of a solution in a microchannel of the microfluidic device. FIG. 20 shows a flowchart of an illustrative embodiment of a method for detecting an analyte or a concentration of a solution in a microchannel of a microfluidic device. It should be understood that for this and other processes and methods disclosed herein, the flowchart shows functionality and operation of one possible implementation of present embodiments. In this regard, some blocks in the flowchart may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example.

Initially, a sample is passed through a microchannel of the microfluidic device, as shown at block 2002. Following, or at the same time, light is transmitted through an optical waveguide that is adjacent a portion of the microchannel, as shown at block 2004. For example, the optical waveguide may comprise a first substantially linear section, a substantially semi-circle section that has a first end coupled to the first substantially linear section, and a second substantially linear section coupled to a second end of the substantially semi-circle section, and the optical waveguide may receive the light via the first section and guide the light through the substantially semi-circle section to the second section. A pathway of the portion of the microchannel is defined by a shape of the substantially semi-circle section so that an evanescent field of the light extends from the semi-circle section into the microchannel.

A change is detected in light output power at an end of the second substantially linear section due to absorbance of a portion of an evanescent field of the light that extends from the substantially semi-circle section decreasing an intensity of the light, as shown at block 2006.

A concentration of the sample in the microchannel can be determined based on the change in light output power, as shown at block 2008. In addition, changes in refractive index of the sample flowing in the microchannel can be detected by changes in light output power. Fore example, referring back to the example outputs shown in FIGS. 10-11, a curve of change in absorbance vs. change in concentration is illustrated. An unknown concentration can be determined by viewing the absorbance change or light output power, for example.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

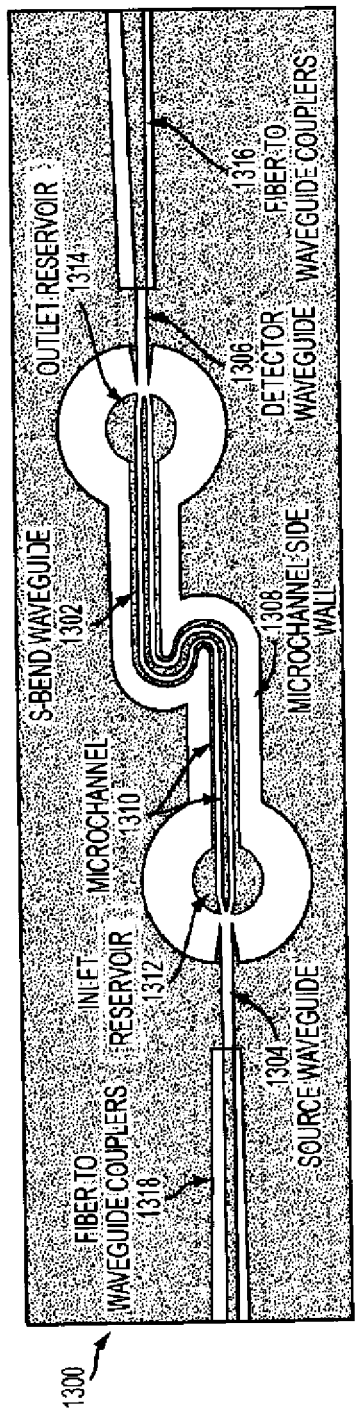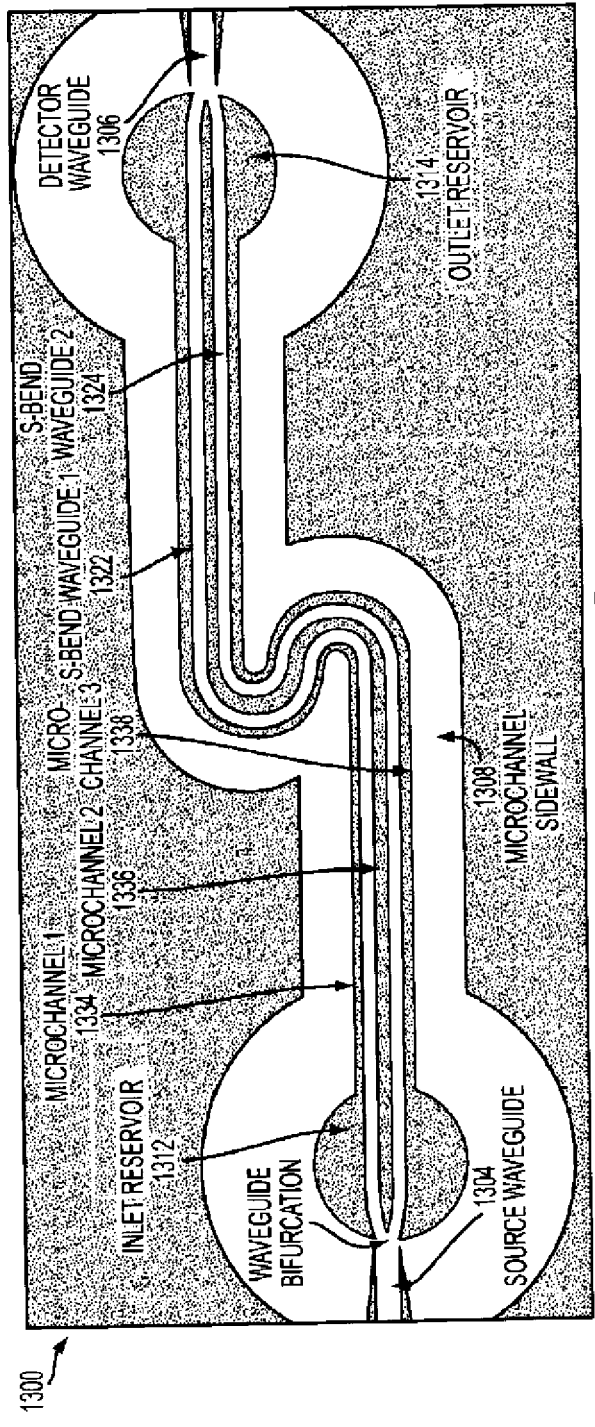

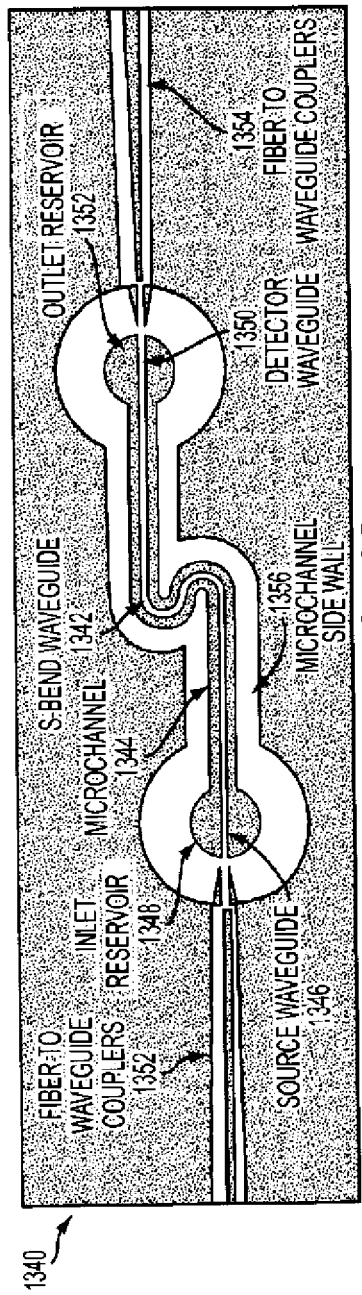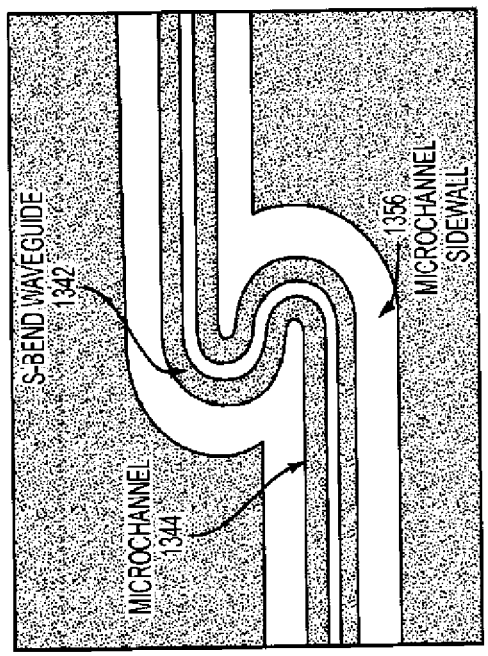

What is claimed is:

1. A microfluidic device comprising:
an optical waveguide that comprises a first substantially linear section, a substantially semi-circle section having a first end coupled to the first substantially linear section, and a second substantially linear section coupled to a second end of the substantially semi-circle section, wherein the optical waveguide is configured to receive an optical beam via the first substantially linear section and to guide the received optical beam through the substantially semi-circle section to the second substantially linear section; and
a microchannel adjacent to the optical waveguide and having a pathway defined by a shape of the optical waveguide, and configured such that a portion of an evanescent field of the received optical beam is configured to extend from the substantially semi-circle section to the microchannel.

2. The microfluidic device of claim 1, further comprising:
a plurality of optical waveguides, each of the plurality of optical wave guides comprising a first substantially linear section, a substantially semi-circle section having a first end coupled to the first substantially linear section, and a second substantially linear section coupled to a second end of the substantially semi-circle section, wherein each of the plurality of optical waveguides is configured to receive an optical beam via the first section and guide the optical beam through the substantially semi-circle section to the second section; and
wherein the pathway of the microchannel is further defined by the substantially semi-circle section of each of the plurality of optical waveguides.

3. The microfluidic device of claim 2, further comprising a plurality of microchannels, wherein each of the plurality of microchannels has a pathway defined by one of the plurality of optical waveguides.

4. The microfluidic device of claim 1, wherein the substantially semi-circle section is coupled to the second substantially linear section via a second substantially semi-circle section.

5. The microfluidic device of claim 4, wherein the first substantially semi-circle section curves in a first direction and the second substantially semi-circle section curves in a second direction opposite the first direction.

6. The microfluidic device of claim 4, wherein the first substantially semi-circle section and the second substantially semi-circle section form an S-shape.

7. The microfluidic device of claim 4, further comprising a plurality of optical waveguides, each of the plurality of optical wave guides comprising a first substantially linear section, a substantially semi-circle section having a first end coupled to the first substantially linear section, and a second substantially linear section coupled to a second end of the substantially semi-circle section via a second substantially semi-circle section, wherein each of the plurality of optical waveguides is configured to receive an optical beam via the first section and guide the optical beam through the substantially semi-circle section to the second section.

8. The microfluidic device of claim 7, further comprising a plurality of microchannels, wherein a pathway of each of the plurality of microchannels is defined by a shape of the optical waveguides, and wherein at least one of the plurality of microchannels is positioned between two optical waveguides.

9. The microfluidic device of claim 1, wherein the first substantially semi-circle section forms a first U-shape waveguide.

10. The microfluidic device of claim 9, further comprising a second U-shape waveguide coupled to the first U-shape waveguide, wherein the first U-shape waveguide is coupled to the second substantially linear section via the second U-shape waveguide.

11. The microfluidic device of claim 1, wherein the microchannel has a width of about 20 μm to about 500 μm.

12. The microfluidic device of claim 1, further comprising a light source coupled to the first substantially linear section to deliver the optical beam.

13. The microfluidic device of claim 1, further comprising a detector coupled to the second substantially linear section to detect an intensity of the optical beam at an end of the second substantially linear section.

14. The microfluidic device of claim 1, wherein the detector is configured to detect light having wavelengths of about 450 nm to about 780 nm.

15. The microfluidic device of claim 1, wherein the optical waveguide has a width of about 200 μm.

16. The microfluidic device of claim 1, wherein changes in refractive index of the sample medium in the microchannel are detected by changes in light output power.

17. The microfluidic device of claim 1, wherein changes in a concentration of a solution in the microchannel are determined by changes in light absorbance output.

18. The microfluidic device of claim 1, wherein the portion of the evanescent field of the optical beam is configured to extend from the substantially semi-circle section to the microchannel thereby decreasing an intensity of the optical beam.

* * * * *

UNITED STATES PATENT AND TRADEMARK OFFICE
CERTIFICATE OF CORRECTION

PATENT NO. : 8,441,645 B2
APPLICATION NO. : 12/984328
DATED : May 14, 2013
INVENTOR(S) : Prabhakar et al.

It is certified that error appears in the above-identified patent and that said Letters Patent is hereby corrected as shown below:

Title Page, Item (56), under "OTHER PUBLICATIONS", in Column 2, Line 15, delete "Slate" and insert -- State --, therefor.

On Title Page 2, Item (56), under "OTHER PUBLICATIONS", in Column 2, Line 22, delete "labon-a-chip." and insert -- lab on a chip, --, therefor.

On Title Page 2, Item (56), under "OTHER PUBLICATIONS", in Column 2, Line 26, delete "devises." and insert -- devices, --, therefor.

In the Drawings:

Delete Drawing Sheets 9 and 10, and replace with Drawing Sheets 9 and 10. (Attached)

In the Specifications:

In Column 20, Line 57, delete "Fore" and insert -- For --, therefor.

Signed and Sealed this
Seventeenth Day of September, 2013

Teresa Stanek Rea
*Deputy Director of the United States Patent and Trademark Office*